US008633161B2

(12) United States Patent
Perrotti et al.

(10) Patent No.: US 8,633,161 B2
(45) Date of Patent: *Jan. 21, 2014

(54) THERAPEUTIC AGENTS FOR THE TREATMENT OF LEUKEMIA

(75) Inventors: Danilo Perrotti, Dublin, OH (US); Paolo Neviani, Columbus, OH (US); Ramasamy Santhanam, Columbus, OH (US); John C. Byrd, Arlington, OH (US); Guido Marcucci, Powell, OH (US); Natarajan Muthusamy, Galloway, OH (US); Ching-Shih Chen, Upper Arlington, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 1161 days.

This patent is subject to a terminal disclaimer.

(21) Appl. No.: 11/909,559

(22) PCT Filed: Mar. 24, 2006

(86) PCT No.: PCT/US2006/010882
§ 371 (c)(1),
(2), (4) Date: May 18, 2010

(87) PCT Pub. No.: WO2006/102611
PCT Pub. Date: Sep. 28, 2006

(65) Prior Publication Data
US 2010/0256072 A1  Oct. 7, 2010

Related U.S. Application Data

(60) Provisional application No. 60/665,091, filed on Mar. 24, 2005.

(51) Int. Cl.
*A61K 38/16* (2006.01)

(52) U.S. Cl.
USPC .......................... 514/19.6; 514/424

(58) Field of Classification Search
None
See application file for complete search history.

(56) References Cited

U.S. PATENT DOCUMENTS

| 4,751,224 | A | 6/1988 | Agarwal et al. |
|---|---|---|---|
| 6,121,329 | A | 9/2000 | Fujii et al. |
| 6,476,004 | B1 | 11/2002 | Sakai et al. |
| 6,624,154 | B1 | 9/2003 | Benoit et al. |
| 2005/0215531 | A1* | 9/2005 | Baumruker et al. .......... 514/114 |

OTHER PUBLICATIONS

Holland-Frei Cancer Medicine 6th Edition, 2003. Tyrosine Kinase Inhibiors: Targeting Considerations. Retreived online at: http://www.ncbi.nlm.nih.gov/books/NBK13641/.*
Laneuville et al. Clonal Evolution in a Myeloid Cell Line Transformed to Interleukin-3 Independent Growth by Retroviral Transduction and Expression of p201 bcr/abl. 1992.*

(Continued)

*Primary Examiner* — Scott Long
*Assistant Examiner* — Sarah Alawadi
(74) *Attorney, Agent, or Firm* — Tarolli, Sundheim, Covell & Tummino L.L.P.

(57) ABSTRACT

The invention provides for methods of treating a mammal who has a BCR/ABL-mediated leukemia, including chronic myelogenous leukemia (CML), particularly the blast crisis stage of CML, Philadelphia-positive acute lymphoblastic leukemia (Ph'-ALL), and refractory leukemias. The invention also provides for compounds for the treatment of these leukemias and methods of identifying anti-leukemic agents.

5 Claims, 18 Drawing Sheets

(56) References Cited

OTHER PUBLICATIONS

Yoshida et al. Journal of Hematology. Biology of Chronic Myeloid Leukemia and Possible Therapeutic Approaches to Imatinib-Resistant Disease. (Mar. 2004).*

International Search Report, PCT/US2006/010882, Mailed Feb. 9, 2007.

Matsuoka et al., "A novel immunosuppressive agent FTY720 induced Akt dephosphorylation in leukemia cells", British Journal of Phamacology, 138: 1303-1312, 2003.

Jamieson et al., "BCR/ABL expression by highly purified chronic myelogenous leukemia hematopoietic stem cells and myeloid progenitors pre- and post-Imatinib therapy", Blood, 101, 418a (2003).

Carlson et al., "Expression of SET, an inhibitor of protein phosphatase 2A, in renal development and Wilms' tumor", J. Am. Soc. Nephrol. 9 (1998), pp. 1873-1880.

Adler et al., "HRX leukemic fusion proteins form a heterocomplex with the leukemia-associated protein SET and protein phosphatase 2A", J. Biol. Chem. 272, 28407-14 (1997).

Li et al., "The myeloid leukemia-associated protein SET is a potent inhibitor of protein phosphatase 2A", J. Biol. Chem. 271 (1996), pp. 11059-11062.

Schonthal, A.H, "Role of serine/threonine protein phosphatase 2A in cancer", Cancer Lett. 170 (2001), pp. 1-13.

Chen et al., "Identification of specific PP2A complexes involved in human cell transformation", Cancer Cell 5, 127-36 (2004).

Feschenko et al., "A novel cAMP-stimulated pathway in protein phosphatase 2A activation", J. Pharmacol. Exp. Ther. 302 (2002), pp. 111-118.

Leibovich et al., "Protamine sulfate inhibition of serum-induced mitogenic responses: differential effects on normal and neoplastic cells",J. Natl. Cancer Inst. 73, 1337-47, Dec. 1984.

Moon et al., "PDE4 inhibitors activate a mitochondrial apoptotic pathway in chronic lymphocytic leukemia cells that is regulated by protein phosphatase 2A", Blood 101 (2003), pp. 4122-4130.

Hu et al., "Requirement of Src kinases Lyn, Hck and Fgr for BCR-ABL1-induced B-lymphoblastic leukemia but not chronic myeloid leukemia", Nat. Genet. 36,453-61 (2004).

Donato et al., "BCR-ABL independence and LYN kinase overexpression in chronic myelogenous leukemia cells selected for resistance to STI571", Blood 101,690-8 (2003).

Lim et al., "BCR/ABL inhibition by an escort/phosphatase fusion protein", Proc. Natl. Acad. Sci. USA 97 (2000), pp. 12233-12238.

Fellner et al., "A novel and essential mechanism for determining specificity and activity of protein phosphatase 2A (PP2A) in vivo", Genes Dev. 17,2138-50 (2003).

Agarwal et al., "Forskolin: a potential antimetastatic agent", Int. J. Cancer 32 (1983), pp. 801-804.

Tzanakakis et al., "Inhibition of hepatic metastasis from a human pancreatic adenocarcinoma (RWP-2) in the nude mouse by prostacyclin, forskolin, and ketoconazole" Cancer 65,446-51 (1990).

Maruno et al., "Vasoactive intestinal peptide inhibits human small-cell lunch cancer proliferation in vitro and in vivo", Proc. Natl. Acad. Sci. U.S.A. 95 14373-8 (1998).

Taetle et al., Further studies on mechanisms of abnormal prostaglandin response by chronic myelogenous leukaemia granulocyte/macrophage progenitors, Leuk. Res. 8 (1984), pp. 833-842.

Gutzkow et al., "Forskolin—mediated G1 arrest in acute lymphoblastic leukaemia cells: phosphorylated pRB sequesters E2Fs", J. Cell Sci. 115 (2002), pp. 1073-1082.

International Search Report for PCT/US07/12921, mailed Dec. 12, 2007.

Sontag, E., "Protein phosphatase 2A: the Trojan Horse of cellular signaling" Cell Signal 13, 7-16 (2001).

Nishikawa et al., "Expression of the catalytic and regulatory subunits of protein phosphatase type 2A may be differentially modulated during retinoic acid-induced granulocytic differentiation of HL-60 cells", Cancer Res. 54, 4879-4884 (1994).

Tawara et al., "Down-regulation by retinoic acid of the catalytic subunit of protein phosphatase type 2A during granulocytic differentiation of HL-60 cells", FEBS Lett, 321, 224-228 (1993).

Salesse et al., "BCR/ABL—mediated increased expression of multiple known and novel genes that may contribute to the pathogenesis of chronic myelogenous leukemia", Molecular Cancer Therapeutics, v. 2, p. 173-182 (2003).

* cited by examiner

THERAPEUTIC AGENTS FOR THE TREATMENT OF LEUKEMIA

REFERENCE TO RELATED APPLICATION

This application is a 371 of PCT/US2006/010882, filed Mar. 24, 2006, and claims priority from U.S. Provisional Application Ser. No. 60/665,091, filed Mar. 24, 2005, the entire content of which is incorporated herein by reference.

STATEMENT OF GOVERNMENT SUPPORT

This invention is supported, at least in part, by grant no. CA095512 from the National Cancer Institute, National Institutes of Health, USA; grant no. DAMD17-03-1-0184 from the US Army, CML Research Program, USA; the Elsa Pardee Foundation for Cancer Research and the Lauri Strauss Leukemia Research Foundation. The U.S. government has certain rights in this invention.

BACKGROUND

Leukemias are malignant neoplasms of hematopoietic tissues. These neoplasms are categorized into two predominant forms: chronic and acute. While acute leukemias are characterized by undifferentiated cell populations, chronic leukemias usually present a more mature morphology. In general the pathological impairment of normal hematopoiesis is the hallmark of all leukemias A tight control of kinase and phosphatase activity is fundamental for normal cell growth, survival, and differentiation. Leukemia is often associated with expression of oncoproteins with aberrant kinase activity. By contrast, PP2A, a phosphatase regulating many cellular functions, is genetically or functionally inactivated in many types of cancer.

Suppression of PP2A activity appears to be a common event in malignant transformation. Moreover, cellular transformation by the SV40 viral oncoprotein small t Ag requires inactivation of PP2A (Yang et al., Control of protein phosphatase 2A by simian virus 40 small-t antigen, *Mol. Cell. Biol.* 11 (1991), pp. 1988-1995), and PP2Ac overexpression reduces Ha-RAS-induced cell transformation (Z. Baharians and A. H. Schonthal, Reduction of Ha-ras-induced cellular transformation by elevated expression of protein phosphatase type 2A, Mol. *Carcinog.* 24 (1999), pp. 246-254). The role of PP2A depends on its ability to interact with and dephosphorylate several factors implicated in the regulation of cell cycle progression, proliferation, survival, and differentiation (E. Sontag, Protein phosphatase 2A: the Trojan Horse of cellular signaling, *Cell. Signal.* 13 (2001), pp. 7-16). The catalytic subunit of PP2A has been linked to retinoic acid-induced cellular differentiation of HL-60 cells, an acute promyelocytic leukemia (APL) cell line (Nishikawa et al., *Cancer Res.*, 1994, 54, 4879-4884; Tawara et al., *FEBS Lett.*, 1993, 321, 224-228).

Forskolin is the chemical active ingredient extracted from the roots of *Coleus Forskohlii*. This natural product has been traditionally used in Hindu traditional medicine to treat asthma, heart disease, glaucoma and more. It is currently used in Japan to treat patients with cardiomyopathy and brochospasm. In addition, there are several lines of evidence showing the in vivo and in vitro anti-tumor activity of this compound against several solid tumor and leukemic cell lines. Forskolin, a diterpene, is a potent activator of adenylate cyclase that has been used extensively to increase intracellular cAMP levels and to elicit cAMP-dependent physiological responses. (e.g. WO 2004/062671). Others have reported the synergistic activity of forskolin, as a known phosphatase kinase A (PKA) agonist, with retinoid X or retinoid acid receptor agonists useful in the treatment of APL or breast cancer. (e.g. U.S. Pat. No. 6,624,154).

Chronic Myelogenous Leukemia (CML)

CML arises when two chromosomes, 9 and 22, mistakenly exchange genetic material during cell division. This translocation t(9;22)(q34;q11), designated as the Philadelphia chromosome (Ph[1]), creates a new, fused gene (called BCR-ABL), that produces an oncogenic enzyme called Bcr-Abl. Bcr-Abl permanently turns on cell growth signals that are normally held in check by phosphatases, and the result is the uncontrolled production of white blood cells.

The clinical course of CML involves the progression from a stable syndrome "chronic phase" (CML-CP) to an acute and fatal stage "blast crisis" (CML-BC) marked by the clonal expansion of an immature population of differentiation-arrested myeloid blasts. BCR/ABL induces and sustains the leukemic phenotype through its deregulated tyrosine kinase activity, which is essential for the recruitment and activation of multiple pathways that transduce oncogenic signals leading to growth factor-independent proliferation, increased survival and altered differentiation of myeloid precursors. Dependence on BCR/ABL expression is not only a characteristic of CML-CP; in fact, levels of BCR/ABL often increase during disease progression and sustained BCR/ABL expression in myeloid progenitor cell lines induces phenotypic changes (i.e. suppression of granulocytic differentiation) characteristic of blast crisis CML.

The goal in treating CML is to eliminate cells containing the Philadelphia chromosome, achieving a complete remission. Stem cell transplantation, when possible, has been the therapy most likely to enable patients with CML to achieve long-term complete remissions. In the past, treatments regimens included chemotherapy (such as with interferon-alpha, hydroxyurea, busulfan). Nowadays the main treatment option for CML patients is imatinib mesylate (Gleevec™, formerly STI571, Novartis). Other potential treatments include dasatinib (Bristol-Myers Squibb, formerly known as BMS-354825) and AMN107 (Novartis). Specific inhibition of BCR/ABL kinase activity with imatinib mesylate is effective not only in the therapy of chronic phase CML but also, albeit temporarily, of accelerate and blastic phase CML, in which imatinib resistance and relapses are contingent to reactivation of BCR/ABL activity. Since this therapy is only a few years old, it is unknown at this time if the complete remissions achieved with this therapy will be as long lasting as the cases after successful stem cell transplant and if progression of CML into blast crisis is prevented.

The main problem with imatinib treatment is the development of resistance and relapse of the disease, which at this moment is considered a factor that favors progression into the fatal blast crisis stage. Main mechanisms of resistance are point mutations, amplification and increased expression of the BCR/ABL oncogene. One of the more problematic mutations is the BCR/ABL T315I mutation, and it is responsible for about 15 percent of cases in which CML patients develop resistance to imatinib. The T315I mutation also confers resistance to dasatinib and AMN107. Dasatinib and AMN107, reportedly can overcome some more than fifty mutations that cause resistance to imatinib, with the exception of T315I. So, it is of particular importance to find a drug that can treat patients with CML harboring the T315I BCR/ABL mutant.

Philadelphia Positive Acute Lymphoblastic Leukemia (Ph[1]-ALL)

It has been recognized for many years that some patients presenting with acute leukemia may have a cytogenetic abnormality that is morphologically indistinguishable from the Philadelphia chromosome (Ph[1]). (See Peterson L C, Bloomfield C D, Bruning R D: Blast crisis as an initial or terminal manifestation of chronic myeloid leukemia: a study of 28 patients. *Am J Med* 60(2): 209-220, 1976.) The Ph[1] occurs in about 30% of adults and a small percentage of children with ALL. (See Seeker-Walker L M, et al.: Variable Philadelphia breakpoints and potential lineage restriction of bcr rearrangement in acute lymphoblastic leukemia. *Blood* 72 (2): 784-91, 1988.) In the majority of children and in more than one half of adults with Ph[1]-positive ALL, the molecular abnormality (known as p190 BCR/ABL) is different from that in Ph1-positive CML (known as p210 BCR/ABL).

The Ph[1] chromosome may be detected using cytogenetic methods to find the chromosome and the translocation. However, many patients who have molecular evidence of the BCR/ABL fusion gene, which characterizes the Ph[1], have no evidence of the abnormal chromosome by cytogenetics. Because many patients have a different fusion protein from the one found in CML (p190 versus p210), the BCR/ABL fusion gene may be detectable only by pulsed-field gel electrophoresis or reverse-transcriptase polymerase chain reaction (RT-PCR). These tests should be performed whenever possible in patients with ALL, especially those with B-cell lineage disease. BCR/ABL rearranged leukemias that do not demonstrate the classical Ph[1] carry a poor prognosis that is similar to those that are Ph[1]-positive. (See Chromosomal abnormalities and their clinical significance in acute lymphoblastic leukemia. Third International Workshop on Chromosomes in Leukemia. *Cancer Res* 43 (2): 868-73, 1983.)

Ph[1]-ALL represents 40% of ALL cases in patients over the age of 40 years. Adults with Ph[1]-ALL, have a poor prognosis and survival at 3 years does not exceed 20% in most studies.

There is a great need for the development of agents for the treatment of BCR/ABL-mediated leukemia patients, particularly those who have developed resistance to therapy, those in the advanced stages of CML or for those with Ph[1]-ALL.

SUMMARY

The invention provides for methods of treating a mammal who has a BCR/ABL-mediated leukemia. Such BCR/ABL-mediated leukemias include CML, particularly in its blast crisis stage, and Ph[1]-ALL.

Accordingly, one embodiment of the invention contemplates treating a BCR/ABL-mediated leukemia in a mammal by administering a PP2A phosphatase activating compound other than imatinib. PP2A activators include, but are not limited to, protamine sulfate, rolipram, forskolin, butyryl-forskolin, 1,9-dideoxy-forskolin, FTY720 and FTY720 derivatives D1 and D2.

According to another embodiment, the mammal has refractory leukemia.

In another embodiment, the mammal is in the blast crisis stage of CML.

Other embodiments include methods for identifying anti-leukemic agents by assessing the ability of agents to activate PP2A phosphatase activity, upregulate the expression of the PP2A catalytic subunit, or downregulate the expression of SET.

Other embodiments of the invention include pharmaceutical compositions for treatment of patients with BCR/ABL-mediated leukemias, including CML and Ph[1]-ALL. In some embodiments the patients are refractory to other treatments.

DETAILED DESCRIPTION

Figure 1:
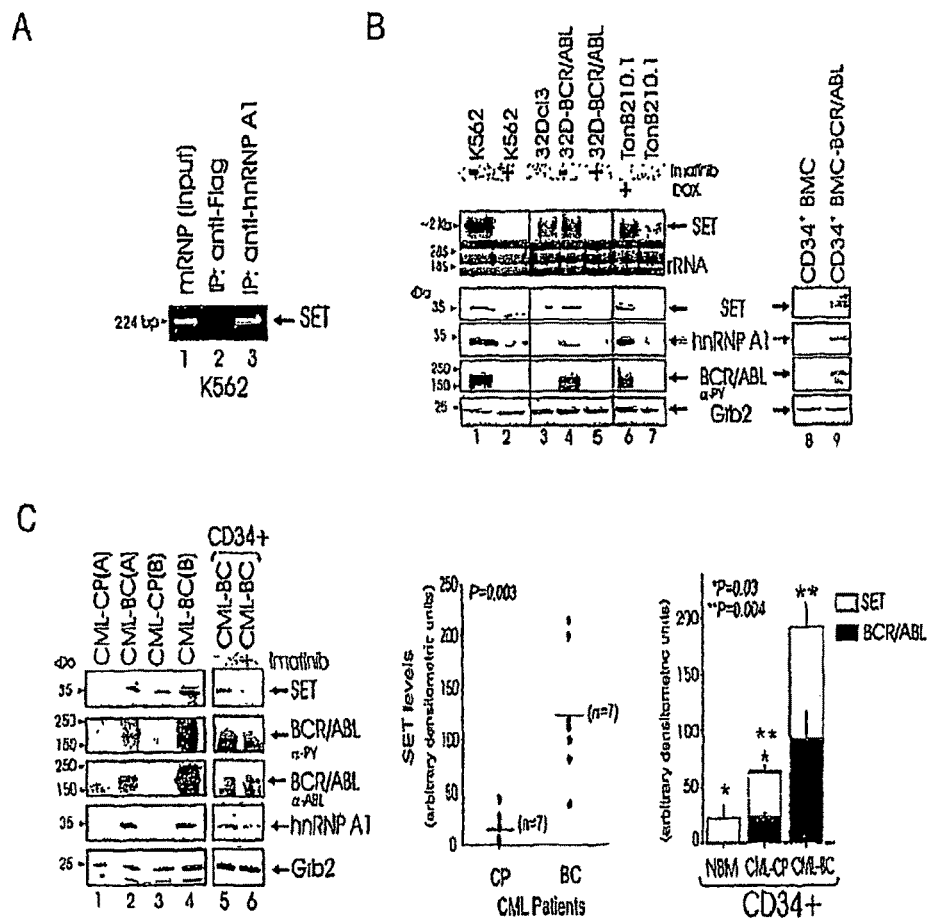
FIG. 1. Effect of BCR/ABL on SET expression. A: RT-PCR shows association of SET mRNA with hnRNP A1 in mRNP-enriched lysates, anti-FLAG-IP (negative control), and anti-hnRNP A1-IP from K562 cells. B: SET RNA (first row) and protein (third row) levels in 32Dc13, untreated and imatinib-treated 32D-BCR/ABL and K562 cells, doxycycline (DOX)-treated or untreated BCR/ABL-inducible TonB210.1 cells, and vector- and BCR/ABL-infected mouse CD34+/lin− bone marrow cells (BMC). hnRNP A1, BCR/ABL, and Grb2 protein levels were detected as control. C: Left panel: SET, hnRNP A1, and BCR/ABL protein levels in mononuclear marrow (BM) cells from two paired CML-CP and -BC patient samples, and in untreated and imatinib-treated CML-BC$^{CD34+}$ cells; middle panel: scatter plots show SET protein levels in BM cells from seven CML-CP and -BC patient specimens (p=0.003; Wilcoxon rank sum test); right panel: graph shows SET (light bars) and BCR/ABL (dark bars) protein expression (expressed as mean±SE of densitometric units after normalization with Grb2 levels) in the CD34+ fraction from bone marrow of healthy donors (NBM) (n=3), CML-CP (n=3), and CML-BC (n=3) patients (NBM versus CML-CP, p=0.03; CML-CP versus CML-BC, p=0.004; paired samples t test).

The present invention provides a novel method for treating BCR/ABL-mediated leukemias in a mammal. Such leukemias include chronic myelogenous leukemia (CML) as well as Philadelphia positive acute lymphoblastic leukemia (Ph$^1$-ALL). The invention also provides for a method of identifying agents that are effective against BCR/ABL mediated leukemias by enhancing and restoring protein phosphatase 2A (PP2A) activity in cells to normal levels. The invention also provides for pharmaceutical compounds for use in treating patients with leukemia. In particular, the invention contemplates the use of PP2A activators to treat BCR/ABL-mediated leukemias in patients who are resistant to imatinib therapy, patients in the blast crisis stage of CML, and patients with Ph$^1$-ALL.

All publications, patent applications, patents, internal web pages and other references mentioned herein are expressly incorporated by reference in their entirety. When the definitions of terms in incorporated references appear to differ from the definitions provided in the present teachings, the definitions provided in the present teachings shall control.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

The invention will now be described with reference to examples. It is known that PP2A is an abundant serine/threonine phosphatase involved in many cellular events including protein synthesis, DNA replication, transcription, and metabolism. PP2A is composed of three protein subunits, A, B, and C. Subunit A is a 60-65 kDa structural component, C is a 36-38 kDa catalytic subunit, and B is a 54-130 kDa regulatory subunit. The core complex of PP2A is comprised of the A and C subunits, which are tightly associated. This dimeric core can be complexed with the regulatory B subunit, which alters the substrate specificity of the PP2A holoenzyme.

The examples cited below show that PP2A activity is suppressed in blast crisis but not chronic phase CML cells through the BCR/ABL-induced expression of its inhibitor, SET. The examples also show that restoration of PP2A activity inhibits BCR/ABL expression/activity, hence impairing both wild-type and T315I BCR/ABL leukemogenesis. The examples further show that PP2A activation results in growth suppression, enhanced apoptosis, restored differentiation, impaired clonogenic potential, and decreased in vivo leukemogenesis of imatinib-sensitive-resistant BCR/ABL$^+$ cells.

These findings establish an unexpected link between an oncogenic kinase and a phosphatase with tumor suppressor activity and indicate that pharmacologic enhancement of PP2A represents a new therapeutic strategy for CML, particularly the blast crisis stage of CML, for the imatinib-resistant CML and Ph$^1$-ALL.

Specifically, the examples show that restoration of PP2A activity back to normal levels via (a) SET downregulation, (b) PP2Ac overexpression, or (c) treatment with potent PP2A activators, such as forskolin, forskolin derivatives, or FTY720 and its derivative compounds, induces marked apoptosis, reduces proliferation, impairs colony formation, inhibits in vivo tumorigenesis/leukemogenesis, and restores differentiation of BCR/ABL-transformed cells regardless of their degree of sensitivity to imatinib. In particular, therapy resistant T315I BCR/ABL+ cells are inhibited by PP2A activation.

Accordingly, one embodiment of the invention contemplates a method for treating BCR/ABL-mediated leukemias in a mammal that involves administering a PP2A phosphatase activating compound other than imatinib. Such BCR/ABL-mediated leukemias include CML and Ph$^1$-ALL. PP2A activators include, but are not limited to, protamine sulfate, rolipram, forskolin, butyryl-forskolin, 1,9-dideoxy-forskolin, FTY720 and FTY720 derivatives D1 and D2. Other derivatives of forskolin and FTY720 with similar PP2A enhancing properties are also within the scope of the invention.

According to one embodiment, the mammal has been previously treated and is resistant to imatinib mesylate (formerly STI-571, now marketed as Gleevac™ or Glivac™, Novartis) or other anti-leukemic agents, including dasatinib (from Bristol-Myers Squibb, formerly known as BMS-354825) and/or AMN107 (Novartis).

In another embodiment, the mammal is in the blast crisis stage of CML.

In another embodiment, other agents capable of activating PP2A phosphatase activity that are suitable for use in the present invention can be identified by evaluating the ability of such agents to (a) upregulate the expression of the PP2A catalytic subunit, or (b) downregulating the expression of SET.

Other embodiments of the invention include pharmaceutical compositions for treatment of patients with BCR/ABL-mediated leukemias, including CML and Ph1-ALL. In some embodiments the patients are refractory to other treatments.

The terms "resistant to imatinib" or "resistant to imatinib therapy" represent a mammal, including a patient, previously treated with imatinib that was either non responsive to treatment with imatinib or had a response to treatment with imatinib and then relapsed.

Similarly, the term "refractory leukemia" represents previously treated patients which were either non responsive to treatment with the agent or had a response to treatment and then relapsed. Such treatments include, but are not limited to, treatment with imatinib, dasatinib, AMN107 or related compounds.

The term "leukemia" represent acute myelogenous leukemia (AML), chronic myelogenous leukemia (CML), acute lymphocytic and/or lymphoblastic leukemia (ALL), including Philadelphia-positive (Ph$^1$) ALL, chronic lymphocytic and/or lymphoblastic leukemia (CLL), hairy cell leukemia (HCL) and all subtypes of these leukemias which are defined by morphological, histochemical, immunological, cytogeneic, molecular or other techniques that are well known by those skilled in the art.

Formulation and Methods of Administration

As used herein, "a pharmaceutically effective amount" is intended an amount effective to elicit a cellular response that is clinically significant, without excessive levels of side effects.

A pharmaceutical composition of the invention is thus provided comprising one or more agents capable of activating PP2A (such as those described above), and a pharmaceutically acceptable carrier or excipient.

The pharmaceutical composition can be administered orally, rectally, parenterally, intrasystemically, intravaginally, intraperitoneally, topically (as by powders, ointments, drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 .mu.m in diameter. Suitable inert carriers include sugars such as lactose. Desirably, at least 95% by weight of the particles of the active ingredient have an effective particle size in the range of 0.01 to 10 .mu.m.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid nonionic surface active agent or can be a solid anionic surface active agent. It is preferred to use the solid anionic surface active agent in the form of a sodium salt.

A further form of topical administration is to the eye. The compounds of the present invention can be delivered in a pharmaceutically acceptable ophthalmic vehicle, such that the compounds are maintained in contact with the ocular surface for a sufficient time period to allow the compounds to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle can be, for example, an ointment, vegetable oil or an encapsulating material.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., Meth. Cell Biol. 14:33 et seq (1976)).

Dosaging

One of ordinary skill will appreciate that effective amounts of the various agents of the invention, agents capable of activating PP2A, can be determined empirically and can be employed in pure form or, where such forms exist, in pharmaceutically acceptable salt, ester or prodrug form. The agents can be administered to a patient in need thereof as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, in the case of forskolin or its derivative compounds, satisfactory results may be obtained by i.v. bolus administration of the compounds at dosages on the order of from 0.05 to 16 mg/kg/day every three days, preferably 0.1 to 7.5 mg/kg/day every three days, more preferably 0.1 to 2 mg/kg/day every three days, in a single dose per day. Oral administration at the same doses is also possible. Suitable daily dosages for patients are thus on the order of from 5 to 250 mg p.o., preferably 5 to 150 mg p.o., more preferably 5 to 75 mg p.o. Dosaging can also be arranged in a patient specific manner to provide a predetermined concentration of the agents in the blood, as determined by techniques accepted and routine in the art (HPLC and mass spectometry assay are preferred). Thus patient dosaging can be adjusted to achieve regular on-going blood levels, as measured by HPLC or mass spectometry, on the order of from 50 to 1000 ng/ml, preferably 150 to 500 ng/ml.

In the case of FTY720 or its derivative compounds, for example, satisfactory results may be obtained by oral administration of the compounds at dosages on the order of from 0.1 to 10 mg/day, preferably 0.1 to 5 mg/day, more preferably 0.1 to 2.5 mg/day, in a single dose per day. I.v. bolus at the same doses is also possible. Dosaging can also be arranged in a patient specific manner to provide a predetermined concentration of the agents in the blood, as determined by techniques accepted and routine in the art (HPLC and mass spectometry assay are preferred). Thus patient dosaging can be adjusted to achieve regular on-going blood levels, as measured by HPLC or mass spectometry.

It will be readily apparent to one of ordinary skill in the relevant arts that other suitable modifications and adaptations to the methods and applications described herein can be made without departing from the scope of the invention or any embodiment thereof.

As described herein, the words "compound" or "composition" are intended to mean a protein, nucleic acid, carbohydrate, lipid or a small molecule.

The following Examples are provided to illustrate various embodiments of the present invention and shall not be considered as limiting in scope.

EXAMPLE 1

The SET/PP2A Interplay in BCR/ABL Leukemogenesis

The example shows a series of experiments that (a) identify SET, a nucleus/cytoplasm-localized phosphoprotein overexpressed in solid tumors and leukemias, as a novel BCR/ABL target whose mRNA is associated with hnRNP A1 in Ph1 cells. The example further shows that in BCR/ABL+ cell lines and in patient-derived CML (CP and BC) CD34+ cells, SET expression is enhanced by BCR/ABL and increases during CML disease progression. This, in turn, results in progressive loss of PP2A tumor-suppressive activity. Restoring PP2A activity in myeloid CML-BC$^{CD34+}$ patient cells and BCR/ABL+ cell lines impairs in vitro and in vivo BCR/ABL leukemogenic potential by inducing inactivation and consequent downregulation of the BCR/ABL oncoprotein itself.

By using chemical inhibitors and activators of PP2A and by interfering with the SET/PP2A interplay (i.e., PP2Ac overexpression, SET knockdown), we provide evidence that BCR/ABL is a bona fide target of PP2A in imatinib-sensitive and -resistant BCR/ABL cell lines and in CML-BCCD34+ patient cells.

Materials and Methods
Cell Cultures and Primary Cells

The Ph$^1$ K562, the BCR/ABL-expressing 32Dc13 and BaF3 cells, and their derivative lines were maintained in culture in IMDM/10% FBS/2 mM L-glutamine. The SET shRNA-, HA-PP2Ac-, and HA-PP2Ac/FLAG-SET-expressing cells were generated by retroviral infection followed by either antibiotic-mediated selection or FACS-mediated sorting of the GFP+ (green fluorescent protein) cells as described (Perrotti et al., (2002), *Nat. Genet.* 30:48-58). The following cells were kind gifts: 32D-p210$^{Y253H}$ (B. Calabretta; TJU, Philadelphia, Pa.); BaF3-p210$^{T315I}$ (B. Druker; OHSU, Portland, Oreg.); TonB210.1 (G. Daley; Harvard University, Cambridge, Mass.). Frozen samples of CD34+ bone marrow cells (NBM) from different healthy donors were from AllCells LLC (Berkeley, Calif.). Frozen samples of mononuclear hematopoietic cells from bone marrow or peripheral blood of unidentifiable CML patients were Ficoll separated and used for Western blot analysis or to isolate the CD34+ fraction by using the CD34 MultiSort kit (Miltenyi Biotec). Before being used in the different assays, CD34+ NBM and CML cells were kept overnight in IMDM supplemented with 50% FBS, 2 mM glutamine, and rhIL-3 (20 ng/ml), rhIL-6 (20 ng/ml), rhFlt-3 ligand (100 ng/ml), and rhKL (100 ng/ml) (Stem Cell Technologies Inc.). Retroviral infection with MSCV-based GFP-containing bicistronic constructs were carried out as described (Iervolino et al., (2002), *Mol. Cell. Biol.* 22: 2255-2266), and infected cells were isolated by FACS-mediated sorting of GFP+ cells. All studies performed with human specimens obtained from The Ohio State University Leukemia Tissue Bank (Columbus, Ohio); from the Division of Hematology, Maisonneuve-Rosemont Hospital (Montreal, Canada); and from Dr. Gambacorti-Passerini (Division of Experimental Oncology, NCI Milan, Italy) were done with approval from The Ohio State University Institutional Review Board. The percentage of CML-CP Ph+ cells by FISH ranged from 91% to 100%. The CML-BC samples were all myeloid blast crisis and, mostly, with complex karyotype; however, no one CML-BC presented deletions of the der9q. Granulocytic differentiation of 32Dc13-derivative cell lines was induced as described (Perrotti et al., (2002), *Nat. Genet.* 30:48-58). Erythroid differentiation of K562 and derivative cell lines was assessed by o-Dianisidine (Fast Blue B; Sigma) staining of methylcellulose colonies. Green/brown-stained cells indicate presence of hemoglobin.

Normal murine hematopoietic marrow cells were obtained from the femurs of wild-type and SHP-1-deficient "viable moth eaten" mice (The Jackson Laboratory). After hypotonic lysis and Ficoll separation, cells were used for the isolation of the CD34+/lin− fraction (Miltenyi Biotech). CD34+ cells were kept for 2 days in complete IMDM supplemented with murine IL-3 (2 ng/ml), IL-6 (1.2 ng/ml), and KL (10 ng/ml) prior to infection with MigRI or MigRI BCR/ABL (W. Pear, University of Pennsylvania, Philadelphia, Pa.). GFP+ (Iervolino et al., 2002) wild-type and SHP-1-/- CD34+ cells ($10^6$) were treated or not with forskolin (40 µM; 48 hr) and used in clonogenic assay or processed for Western blot. Where indicated, cells were treated with the following: ALLN, okadaic acid, calyculin A, SS, and butyryl-forkolin (EMD Bioscience Inc.); forskolin, 1,9-dideoxy-forskolin, and myristoylated PKI-(14-22) amide (BioMol); imatinib (Novartis); and theophylline (Sigma). Cells in liquid culture were treated with forskolin or imatinib at 40 µM and 1 µM, respectively, and a half dose of forskolin or imatinib was added every 18 hr.

Plasmids pHM6-HA-PP2Ac: pHM6-HA-PP2Ac contains the HA-tagged PP2A catalytic subunit under the control of the CMV promoter (P. B. Rothman, Columbia University, New York, N.Y.). MigRI-HA-PP2Ac: The HA-tagged PP2Ac cDNA was PCR amplified from pHM6-HA-PP2Ac and subcloned into the HpaI/EcoRI sites of the bicistronic GFP-containing MigRI vector. pSuper.retro-shSET: The shRNA SET construct was obtained by subcloning the double-stranded 60 mer oligonucleotide containing the SET target sequence (5'-TGAAATAGACAGACTTAAT-3') into the pSuper.retro- .neo+GFP vector (OligoEngine Inc.). MSCV-FLAG-SET: The human SET cDNA was obtained from K562 mRNA by RT-PCR using an upstream primer containing a HpaI site, the FLAG epitope, and the first 16 nucleotides of SET cDNA, and a downstream primer containing the last 21 nucleotides of SET linked to an EcoRI restriction site. The HpaI/EcoRI-digested PCR product was subcloned into the MSCV-puro vector.

RT-PCR of Immunoprecipitated RNA

K562 cells ($10^8$) were lysed in 2 pellet/vol of 10 mM HEPES (pH 7.0), 100 mM KCl, 1 mM $MgCl_2$, 1 mM DTT, 0.5% Nonidet P-40, 100 U/ml RNase OUT (Invitrogen), 0.2 mM PMSF, 1 mg/ml pepstatin A, 5 mg/ml bestatin, and 20 mg/ml leupeptin and clarified (100,000×g, 2.5 hr). RNP-containing particles were purified by centrifugation (300,000×g; 3 hr) and resuspended in 1 ml of 50 mM Tris (pH 7.4), 150 mM NaCl, 1 mM $MgCl_2$, 0.05% NP-40, 100 U/ml RNase OUT, 0.2 mM PMSF, and 20 mM EDTA. Immunoprecipitation (IP) and extraction of the hnRNP A1 bound mRNA was performed as described (Tenenbaum et al., 2002), Methods 26:191-198). The presence of SET transcripts was assessed by RT-PCR performed on an equal amount of RNA, extracted from RNP-enriched lysates (input) as well as from the hnRNP-A1 or FLAG immunoprecipitates. To amplify SET mRNA, the following primers were used: 5'-GAGGTCA-GAATT GATCGCCAAAATC-3' and 5'-TCAGATGAAAT-TCTTTGGAGAGAAC-3'.

Northern Blot Analysis and RT-PCR

Total RNA was isolated using the acid phenol-guanidinium-mediated extraction (Tri-Reagent; Invitrogen). For Northern blot, total RNA (5 µg) was hybridized to $^{32}P$-labeled hSET cDNA. To detect BCR/ABL transcripts, RNA was extracted (QIAamp RNA blood kit; Qiagen) from mouse peripheral blood (100 µl). RNA from K562:32Dcl3 cells (ratio 1:$10^6$) served as positive control, whereas RNA from blood of mice that were not injected with BCR/ABL+ cells was used as negative control. Total RNA (1 µg) was reverse transcribed in 20 µl, and cDNA (5 µl) was used to detect BCR/ABL transcripts by nested PCR using a first set of primers spanning the bcr exon 1/abl exon 3 and a second set amplifying a bcr exon 2/abl exon 3 fragment. The nested RT-PCR conditions were previously described (Cross et al., 1993), Blood 82:1929-1936). GAPDH levels were monitored as control for equal amplification.

Western Blot Analysis and IP

Cells ($10^7$) were lysed in 100 µl of RIPA buffer (150 mM NaCl, 1% NP-40, 0.1% SDS, 50 mM Tris [pH 8.0]) supplemented with 1 mM PMSF, 25 µg/ml aprotinin, 10 µg/ml leupeptin, 100 µg/ml pepstatin A, 5 mM benzamidine, 1 mM $Na_3VO_4$, 50 mM NaF, 10 mM β-glycerol-phosphate. After incubation on ice (30 min), lysates were clarified (12,000×g, 15 min, 4° C.), denatured, and subjected to SDS-PAGE and Western blot (Iervolino et al., 2002). The antibodies used were goat polyclonal anti-SET(I2PP2A), -pp32(I1PP2A), and -hnRNP A1 and rabbit polyclonal anti-SHP-1 (Santa Cruz Biotechnology); monoclonal anti-Abl (Ab-3), -c-myc (Ab-2), -phosphotyrosine PY20 (Ab-4), and -pBAD$^{S112}$ (Ab-1) (EMD); monoclonal anti-hnRNP A1 (9H10) (G. Dreyfuss, University of Pennsylvania, Philadelphia, Pa.); monoclonal anti-GRB2 and -Rb (BD TransLab Inc.); monoclonal anti-HA (Covance); monoclonal anti-PP2Ac, clone 1D6 (Upstate Inc.); monoclonal anti-FLAG, clone M2 (Sigma); monoclonal anti-pERK$^{T202/Y204}$ and rabbit polyclonal anti-pAKT$^{T308}$, pSTAT5$^{Y694}$, -pJak2$^{Y1007/1008}$, -Jak2, -BAD, -Akt, and -ERK1/2 (Cell Signaling Technology Inc.); monoclonal anti-STATS (Invitrogen); rabbit monoclonal anti-pPP2A$^{Y307}$ (Epitomics); rabbit polyclonal anti-PR65/A (Calbiochem). IPs were carried out in 20 mM HEPES (pH 7.0), 150 mM NaCl, and 0.2% NP-40 supplemented with protease and phosphatase inhibitors. Lysates were precleared and immunoprecipitated with Ab-coated beads for 3 hr at 4° C. After washings, IPs were subjected to SDS-PAGE and Western blot.

Phosphatase Assays

PP2A phosphatase assays were carried out using the PP2A IP phosphatase assay kit (Upstate). Briefly, protein lysates (50 µg) in 100 µl of 20 mM HEPES (pH 7.0)/100 mM NaCl, 5 µg of PP2Ac antibody (Upstate), and 25 µl of Protein A-agarose were added to 400 µl of 50 mM Tris (pH 7.0)/100 mM CaCl2, and IPs were carried out at 4° C. for 2 hr. IPs were washed and used in the phosphatase reaction according to the manufacturer's protocol. Specificity of the PP2A assay was assessed by titration with okadaic acid and by ascertaining the absence of PP1a in the PP2A immunoprecipitates (Figure S2A). As internal control, the amount of immunoprecipitated PP2A was also monitored by anti-PP2Ac Western blots (Figure S2B).

Clonogenic Assays

Methylcellulose colony formation assays were carried out by plating 103 or 5×104 cells from BCR/ABL cell lines or primary human CML and mouse BMC, respectively, in 0.9% MethoCult H4230 (Stem Cell Technologies Inc.). Where indicated, cells were plated in the presence of rhIL-3 (100 ng/ml) or rhG-CSF (25 ng/ml). Colonies (>125 µm) from cell lines and primary cells were scored 7 and 15 days later, respectively.

Results

SET Association with hnRNP A1 and Effect of BCR/ABL on SET Expression

Using Ribonomics (Tenenbaum et al., (2002), Methods 26:191-198), SET mRNA was found specifically associated with cytoplasmic hnRNP A1 in Ph$^1$ K562 cells (data not shown). To validate the SET mRNA-hnRNP A1 association, RT-PCR was carried out on anti-hnRNP A1- and anti-FLAG-immunoprecipitated cytoplasmic mRNAs using a pair of primers spanning a 224 bp segment of the human SET cDNA. As shown, high levels of SET mRNA transcripts, similar to those present in the mRNP-enriched mRNA fraction, were clearly detectable in association with hnRNP A1 (FIG. 1A).

In growth factor-independent BCR/ABL-expressing 32Dc13 myeloid precursors, SET mRNA and protein levels correlated with those of hnRNP A1 and BCR/ABL (FIG. 1B). Similarly, SET was upregulated in the doxycycline-treated (2 µg/ml; 3 days) TonB210.1 lymphoid precursors in which BCR/ABL expression is tetracycline inducible (FIG. 1B, lanes 6 and 7). In addition, treatment (24 hr, 1 µM) with the ABL tyrosine kinase inhibitor imatinib markedly impaired SET mRNA and protein expression in both 32D-BCR/ABL and K562 cells (FIG. 1B, lanes 2 and 5). Consistent with these data, SET and hnRNP A1 levels were increased upon BCR/ABL expression in CD34$^+$ mouse bone marrow cells (BMC) (FIG. 1B, lanes 8 and 9).

SET protein levels correlated with BCR/ABL activity and were higher in myeloid CML-BC$^{CD34+}$ (n=3) than CML-CP$^{CD34+}$ (n=3) patient-derived BMC, and in CML-CP$^{CD34+}$ patient cells than in CD34$^+$ cells from normal donors (NBM) (n=3) (FIG. 1C, right panel). Similarly, SET expression was higher in myeloid CML-BC (n=9) than in CML-CP (n=9) patient-derived mononuclear marrow cells (FIG. 1C, left and middle panels) and correlated with that of BCR/ABL and hnRNP A1 in paired CML-CP and CML-BC samples (FIG. 1C, left panel). Moreover, treatment of CML-BC$^{CD34+}$ cells with imatinib decreased SET levels (FIG. 1C, lanes 5 and 6), further indicating that BCR/ABL activity is responsible for SET upregulation in CML-BC. As expected, SET expression was reduced in cytokine-deprived (12 hr) 32Dc13 and NBM$^{CD34+}$ cells (FIG. 8A) but not in cytokine-deprived BCR/ABL$^+$ cells.

Figure 2:
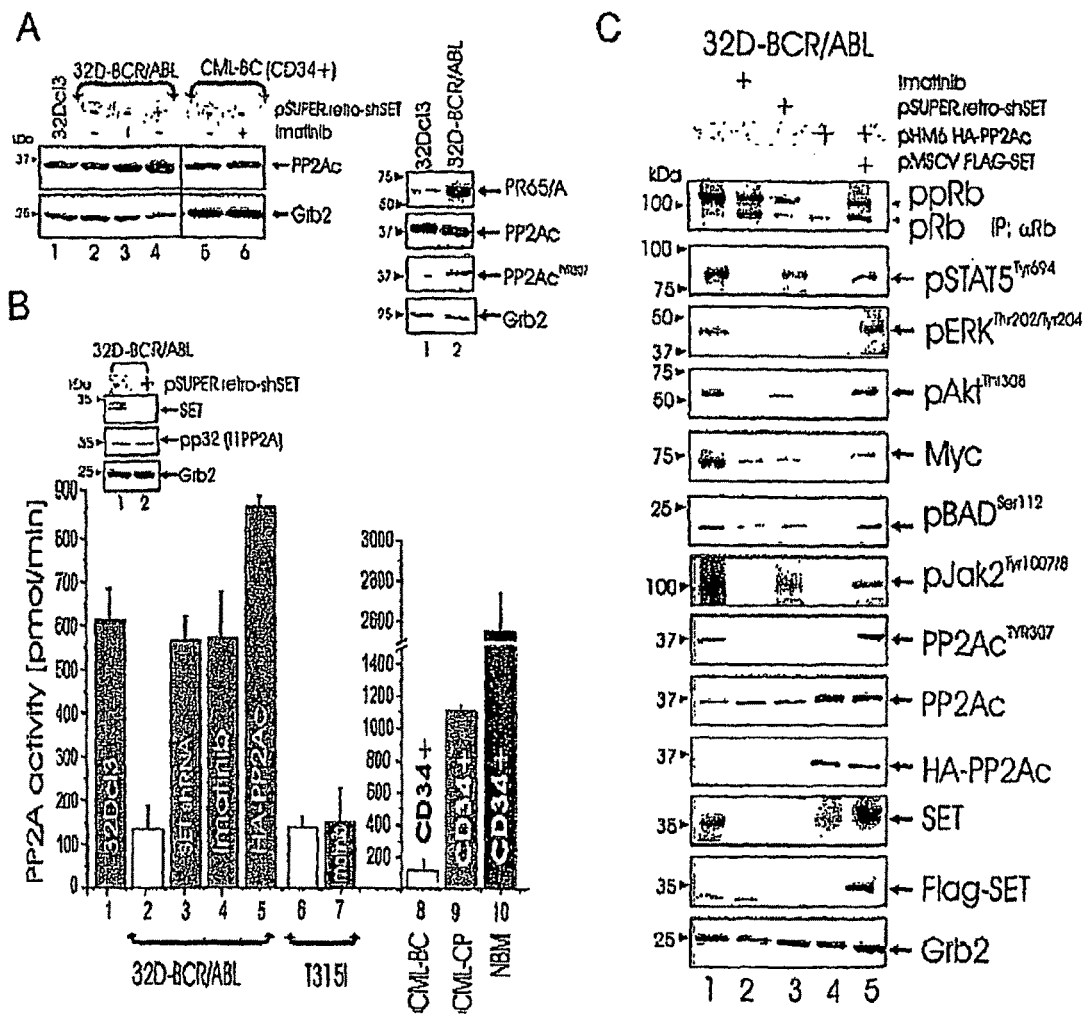
FIG. 2. Effect of BCR/ABL on PP2A activity. A: Left panel: protein levels of PP2Ac and Grb2 in the following: 32Dc13, untreated and imatinib-treated 32D-BCR/ABL and primary CML-BC$^{CD34+}$ marrow cells, and SET shRNA-expressing 32D-BCR/ABL; right panel: levels of PR65/A, PP2Ac, PP2Ac$^{TYR307}$, and Grb2 in 32Dc13 and 32D-BCR/ABL cells. B: PP2A phosphatase assay in 32Dc13, 32D-BCR/ABL, BaF3-p210(T315I), CML-BC$^{CD34+}$, CML-CP$^{CD34+}$, and NBM$^{CD34+}$ cells, and in BCR/ABL cells expressing the SET shRNA or HA-PP2Ac or treated with imatinib. Bars represent the PP2A activity (expressed as mean±SE of three independent experiments performed with the indicated cell lines, and with NBM$^{CD34+}$ (n=3), CML-CP$^{CD34+}$ (n=3), and CML-BC$^{CD34+}$ (n=3) cells. Inset: effect of the SET shRNA on SET and pp32 protein levels; representative of two experiments performed in triplicate. C: Effect of imatinib and of ectopic SET shRNA, HA-PP2Ac, or HA-PP2A/FLAG-SET expression on the levels of the indicated BCR/ABL and PP2A targets in 32D-BCR/ABL cells. Endogenous and ectopic SET and PP2Ac and PP2Ac$^{TYR307}$ levels are shown (rows 8-12).

Relevance of Increased SET Expression in BCR/ABL-Transformed Cells: Role of PP2A SET is a potent inhibitor of the multimeric serine-threonine phosphatase PP2A. In 32D-BCR/ABL and in CML-BC$^{CD34+}$ patient cells (FIG. 2A, left panel) and K562 cells (data not shown), levels of the PP2A catalytic subunit (PP2Ac) were not affected by BCR/ABL expression and/or kinase activity. By contrast, levels of the PP2A structural subunit PR65/A were enhanced in 32D-BCR/ABL cells and correlated with increased levels of PP2Ac phosphorylation on tyrosine 307 (FIG. 2A, right panel) which, inhibits PP2A activity. Accordingly, PP2A activity was reduced by 83% in 32D-BCR/ABL compared to parental 32Dc13 cells, and restored to normal levels in imatinib-treated (1 µM, 24 hr) 32D-BCR/ABL cells (FIG. 2B). Imatinib did not rescue PP2A activity in imatinib-resistant BaF3p210$^{T315I}$ cells (FIG. 2B). Furthermore, PP2A activity was also reduced by 94% and 52% in the CD34$^+$ fraction of myeloid CML-BC and CML-CP cells, respectively, compared to the CD34$^+$ fraction of NBM cells (FIG. 2B).

Figure 8:
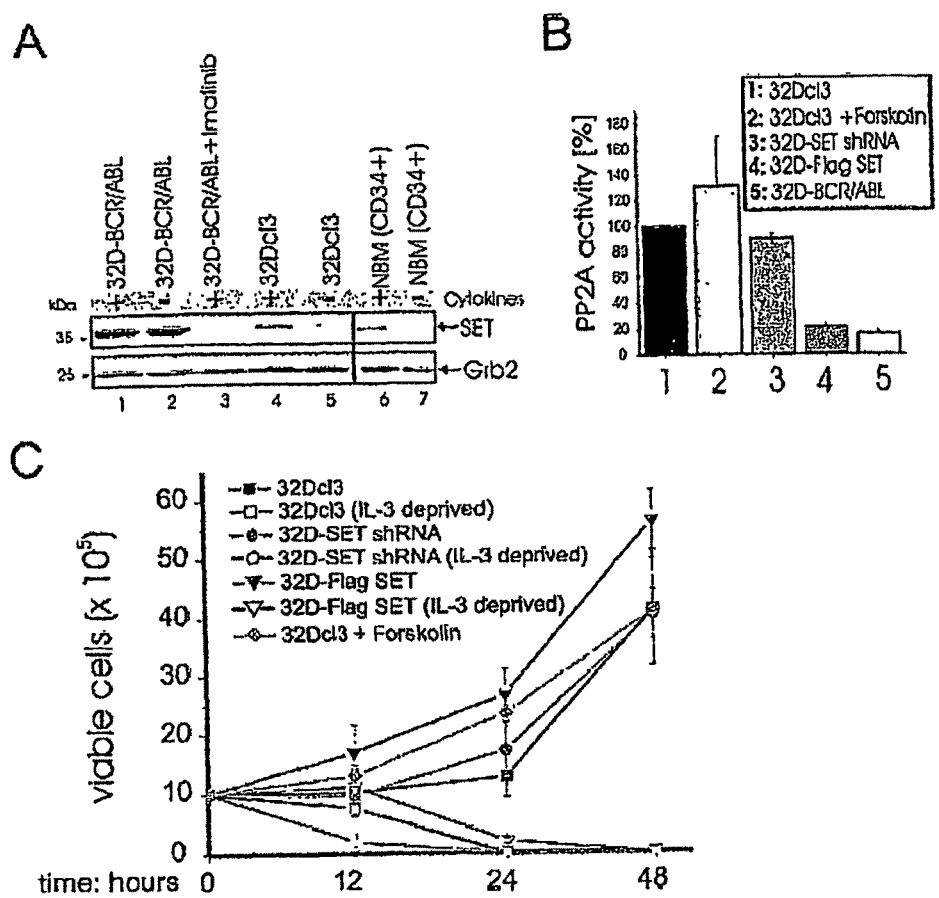
Figure 9:
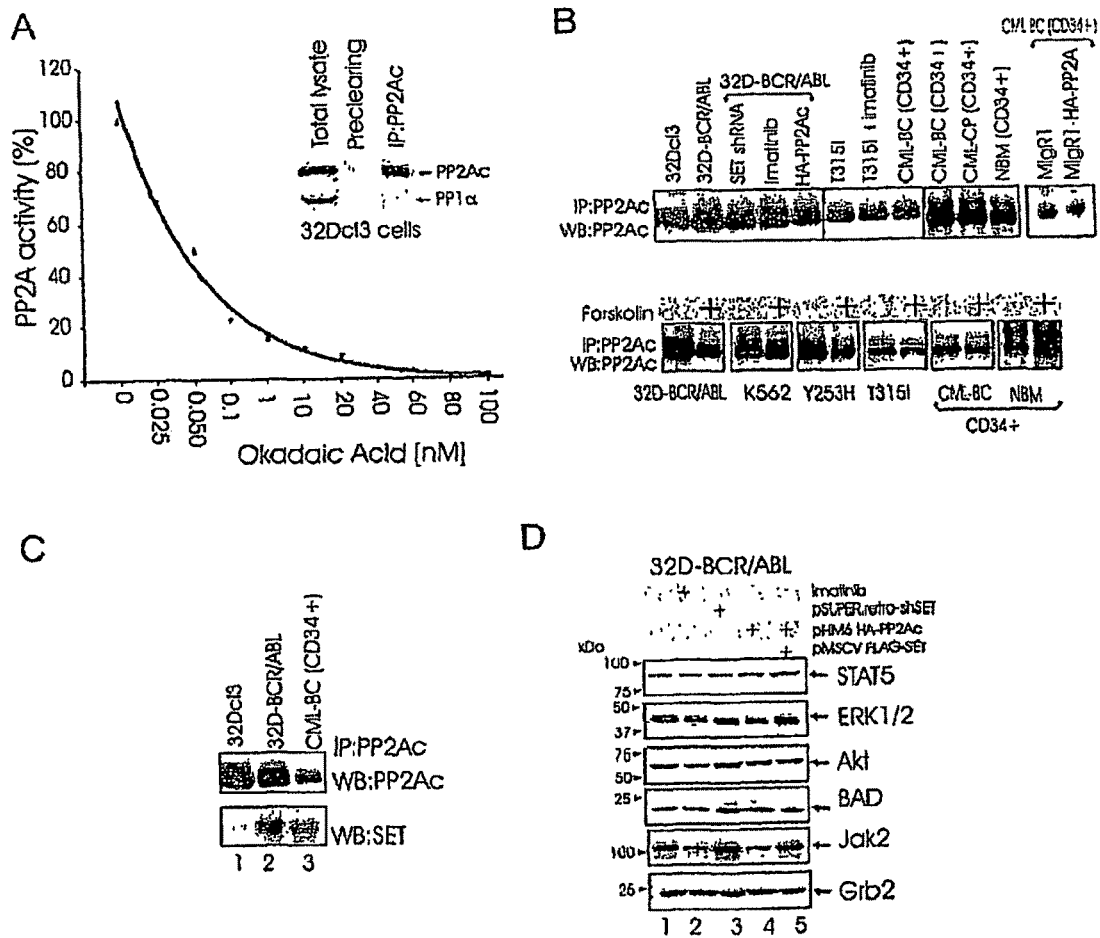
FIG. 9. PP2A expression and activity in different BCR/ABL-expressing cell lines and primary marrow CML cells. A: Effect of okadaic acid on PP2A activity in 32Dc13 cells. Graph shows titration of PP2A phosphatase activity with the phosphatase inhibitor okadaic acid used at the indicated concentration. PP2A activity was assessed on PP2A immunoprecipitates as described in the Materials and Methods. Inset: Western blots show levels of PP2Ac and PP1α in total lysates (lane 1), preclearings (lane 2) and anti-PP2Ac immunoprecipitates (lane 3) from 32Dc13 cells. B: Levels of immunoprecipitated PP2Ac used in phosphatase assays. Western blots anti-PP2Ac show levels of immunoprecipitated PP2Ac from the cell lines and primary cells used in the phosphatase assays showed in FIGS. 2B, 5C and 6A. C: Association of SET with PP2A in BCR/ABL-expressing cells. Western blots show levels of immunoprecipitated PP2Ac and co-immunoprecipitated SET in 32Dc13 and 32D-BCR/ABL cell lines and myeloid CML-BC$^{CD34+}$ patient cells. Note that ratios of PP2A$^{32D-BCR/ABL}$ vs. PP2A$^{CML-BC}$ and SET$^{32D-BCR/ABL}$ vs. SET$^{CML-BC}$ levels estimated by densitometry were 2.31 and 2.44, respectively (not shown). D: Influence of SET and PP2Ac expression on STAT5, ERK1/2, Akt, BAD and Jak2 levels in BCR/ABL transformed cells. Western blots show effect of imatinib, SET downregulation, HA-PP2Ac and HA-PP2Ac/Flag-SET overexpression on the total levels of different BCR/ABL and PP2A targets in 32D-BCR/ABL cells. Grb2 was detected as control for equal loading.

To determine whether SET upregulation is responsible for suppression of PP2A activity, we interfered with SET expression by infecting parental 32Dc13, 32D-BCR/ABL, and K562 cells with a pSuper.retro-shSET construct carrying a short hairpin RNA (shRNA) targeting nucleotides 120-138 of the SET cDNA. Expression of SET shRNA downregulated levels of SET, but not those of the other PP2A regulator pp32/I1PP2A (FIG. 2B, inset) and restored PP2A activity to levels similar to those of 32Dc13 or imatinib-treated 32D-BCR/ABL cells (FIG. 2B) without affecting PP2Ac expression (FIG. 2A). Interestingly, levels of PP2Ac$^{TYR307}$ were markedly reduced upon imatinib treatment and SET downregulation (FIG. 2C). Moreover, in BCR/ABL-expressing cells, expression of ectopic HA-PP2Ac strongly increased PP2A activity (FIG. 2B) and diminished PP2Ac$^{TYR307}$ levels (FIG. 2C), while no effects were observed in vector-transduced cells (data not shown). PP2A activity also was not significantly affected in parental 32Dc13 cells by SET shRNA expression (FIG. 8B). By contrast, ectopic FLAG-SET expression augmented PP2A$^{TYR307}$ levels in HA-PP2Ac-expressing BCR/ABL cells (FIG. 2C) and lowered PP2A activity in 32Dc13 cells to levels similar to those of 32D-BCR/ABL cells (FIG. 8B). Accordingly, SET was associated with PP2Ac in 32D-BCR/ABL and CML-BC$^{CD34+}$ cells but not in 32Dc13 cells (Figure S2C).

Because several PP2A targets are essential for BCR/ABL leukemogenic potential, we assessed the importance of the SET-PP2A interplay in the regulation of the BCR/ABL signaling network by determining the levels and/or activity of distinct BCR/ABL and PP2A targets in SET shRNA- and HA-PP2Ac-expressing 32D-BCR/ABL cells. In these cells, enhanced PP2A activity induced by imatinib treatment, by inhibition of SET, and to a greater extent, by PP2Ac overexpression decreased levels of hyperphosphorylated Rb, suppressed Myc expression, and STAT5, ERK1/2, Akt, BAD, and Jak2 phosphorylation (FIG. 2C, lanes 2-4) without affecting their expression (Figure S2D). Consistent with the role of PP2A as a potent BCR/ABL antagonist, transduction of FLAG-SET in HA-PP2A-expressing 32D-BCR/ABL cells restored the expression/activity of these BCR/ABL targets (FIG. 2C, lane 5).

BCR/ABL is a Target of PP2A Activity

Figure 3:
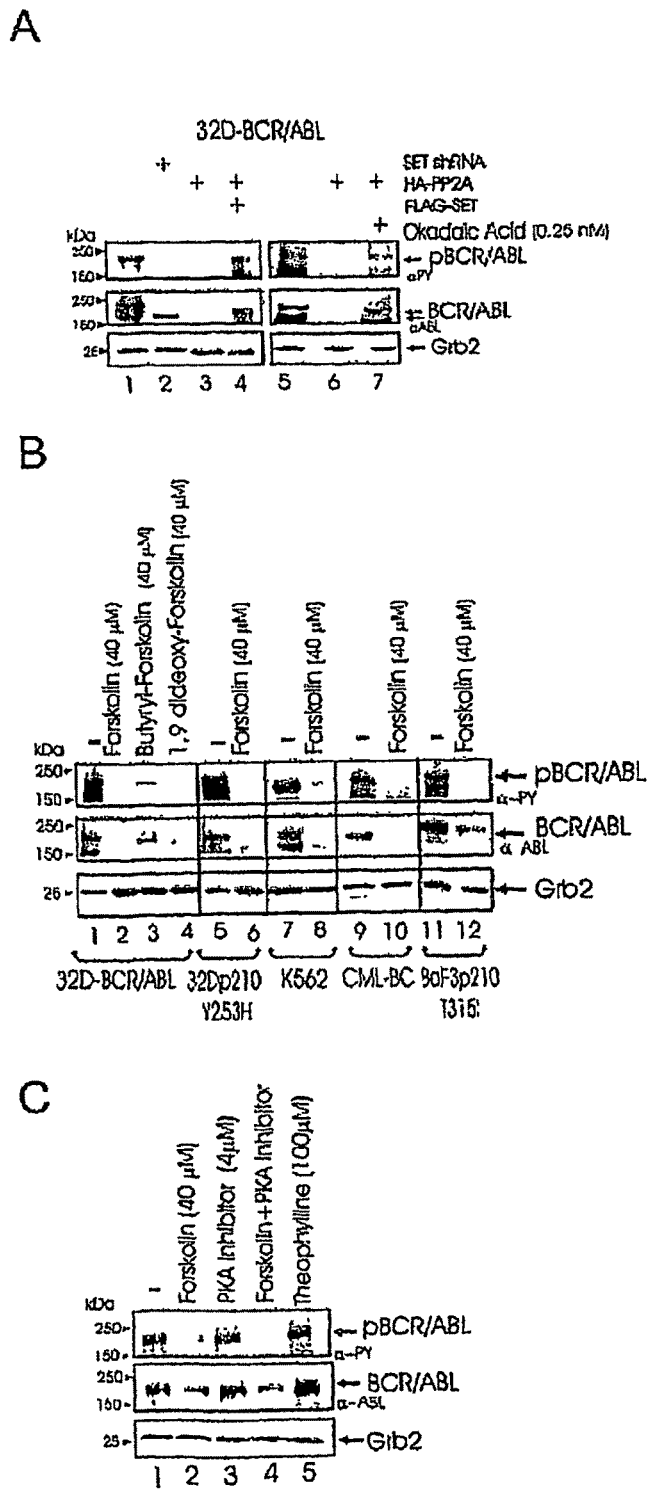
FIG. 3. Effect of PP2A on BCR/ABL kinase activity and expression. A: p210BCR/ABL activity (αPY) and expression (α-Abl) in 32D-BCR/ABL and in its derivative SET shRNA-, HA-PP2A-, and HA-PP2A/FLAG-SET-expressing cell lines, and in HA-PP2A 32D-BCR/ABL cells treated with okadaic acid. B: Effect of the PP2A activators forskolin, butyryl-forskolin, and 1,9-dideoxy-forskolin on BCR/ABL activity and expression in primary CML-BC and imatinib-sensitive and -resistant BCR/ABL cell lines. C: Effects of forskolin, theophylline, and the PKA inhibitor myristoylated PIC (14-22) amide on BCR/ABL expression/activity. Grb2 levels were detected as controls.

Expression of SET shRNA or HA-PP2A in 32D-BCR/ABL cells suppressed p210$^{BCR/ABL}$ tyrosine phosphorylation and expression (FIG. 3A, lanes 2 and 3). This effect, also observed in K562 cells (data not shown), was dependent on enhanced PP2A phosphatase activity because both SET overexpression and treatment with the phosphatase inhibitor okadaic acid (0.25 nM; 1 hr) and calyculin A (data not shown), used at concentrations that inhibit PP2A but not other phosphatases (Saydam et al., (2003), Leuk. Res. 27:709-717), restored BCR/ABL activity and expression in HA-PP2Ac-transduced (FIG. 3A, lanes 4 and 7) and in SET shRNA-transduced (data not shown) cells. Conversely, exposure (18-24 hr) of BCR/ABL$^+$ cell lines and CML-BC$^{CD34+}$ marrow blasts to the PP2A activators forskolin (40 µM), butyryl-forskolin (water soluble), or 1,9-dideoxy-forskolin (lacks adenylate cyclase-activating function) enhanced PP2A activity (Figure S3A), abolished BCR/ABL phosphorylation, and to a different extent, induced downregulation of BCR/ABL (FIG. 3B) with EC$_{50}$ of 18 µM and 25 µM in imatinib-sensitive and -resistant cells, respectively. Interestingly, the cAMP inducer theophylline (100 µM; 24 hr) did not affect BCR/ABL expression/activity, and the PKA inhibitor myristoylated-PKI(14-22)-amide (4 µM; 24 hr) did not inhibit the forskolin-induced BCR/ABL downregulation (FIG. 3C).

PP2A-Dependent Mechanisms Regulating BCR/ABL Expression/Activity

To determine whether PP2A-induced BCR/ABL dephosphorylation renders BCR/ABL more susceptible to proteolysis, we treated PP2A-expressing 32D-BCR/ABL cells with the proteasome inhibitor ALLN (25 µM; 8 hr). As shown, ALLN restored BCR/ABL expression and, as expected, did not prevent PP2A-induced BCR/ABL tyrosine dephosphorylation (FIG. 4A), which precedes and, likely, is required for its degradation.

Figure 4:
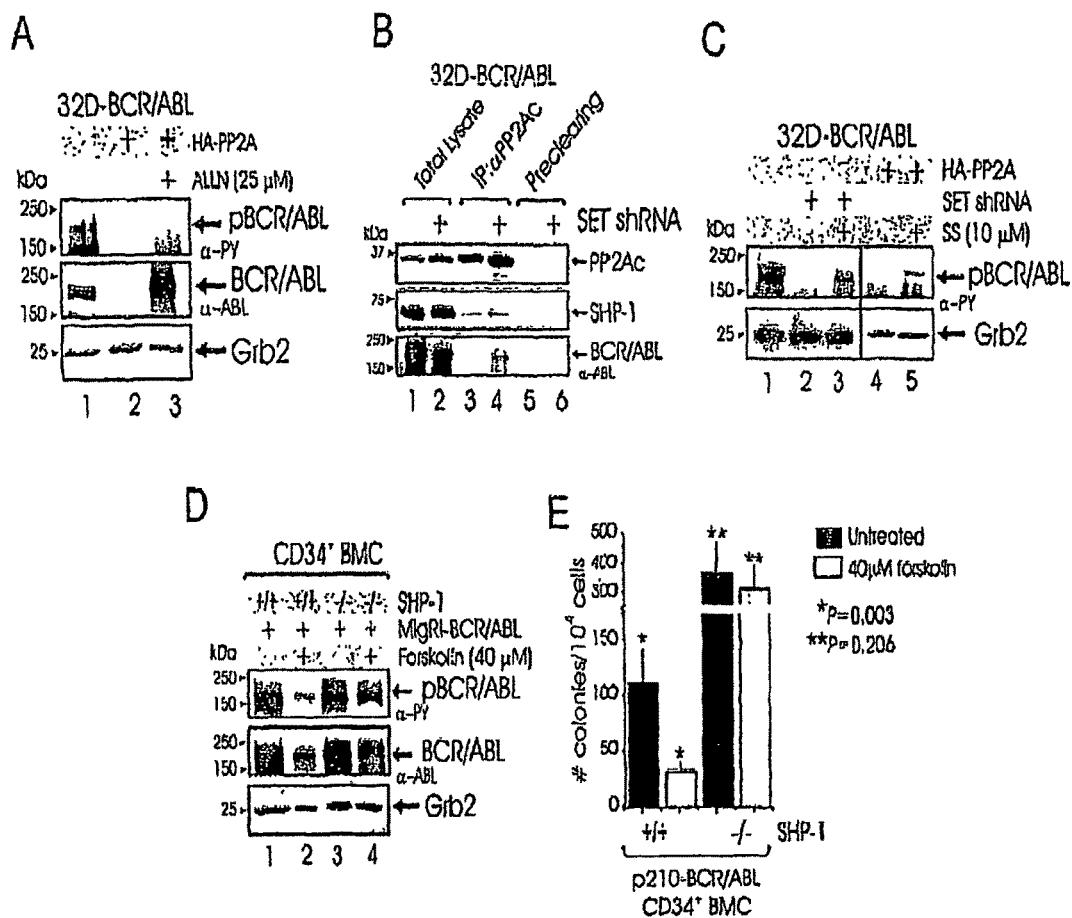
FIG. 4. PP2A-dependent regulation of BCR/ABL activity/expression. A: p210$^{BCR/ABL}$ activity and expression in parental and untreated or ALLN-treated HA-PP2A-expressing 32D-BCR/ABL cells. B: Association of PP2A with BCR/ABL and SHP-1 in parental and SET shRNA-expressing 32D-BCR/ABL cells. C: Effect of the SHP-1 inhibitor sodium stibogluconate (SS) on BCR/ABL activity in parental and HA-PP2A- and SET shRNA-expressing 32D-BCR/ABL cells. Effect of forskolin on BCR/ABL expression/phosphorylation (D) and clonogenicity (E) of BCR/ABL-expressing wild-type (+/+) and SHP-1-deficient "viable moth eaten" (−/−) CD34+ mouse bone marrow cells (BMC). Bars represent the mean±SE of the colony number from four clonogenic assays with untreated and forskolin-treated BCR/ABL-expressing wild-type and viable moth eaten CD34+ marrow cells (untreated+/+ versus drug-treated+/+, p=0.003; untreated−/− versus drug-treated−/− p=0.206; paired samples t test).

In anti-Abl Western blot on anti-PP2Ac immunoprecipitates, we found p210$^{BCR/ABL}$ associated with PP2Ac in SET shRNA-expressing but not in parental 32D-BCR/ABL cells (FIG. 4B, lanes 3 and 4). Interestingly, the BCR/ABL-associated SHP-1 tyrosine phosphatase was also present in the same PP2A-containing complex (FIG. 4B), and restored BCR/ABL phosphorylation was observed after treatment of SET shRNA- and HA-PP2A-expressing 32D-BCR/ABL cells with sodium stibogluconate (SS) (FIG. 4C), a specific SHP-1 inhibitor. Furthermore, the PP2A activator forskolin (40 μM; 18 hr) inhibited BCR/ABL expression and tyrosine phosphorylation and decreased by ~70% the clonogenic potential of BCR/ABL-transduced wild-type (+/+) but not SHP-1-deficient (−/−) moth eaten viable CD34+ mouse marrow cells (FIGS. 4D and 4E). Note that the clonogenicity of SHP-1$^{-/-}$ cells was higher than that of wild-type cells (FIG. 4E).

Increased PP2A Activity Suppresses BCR/ABL Oncogenic Potential In Vitro

Figure 5:
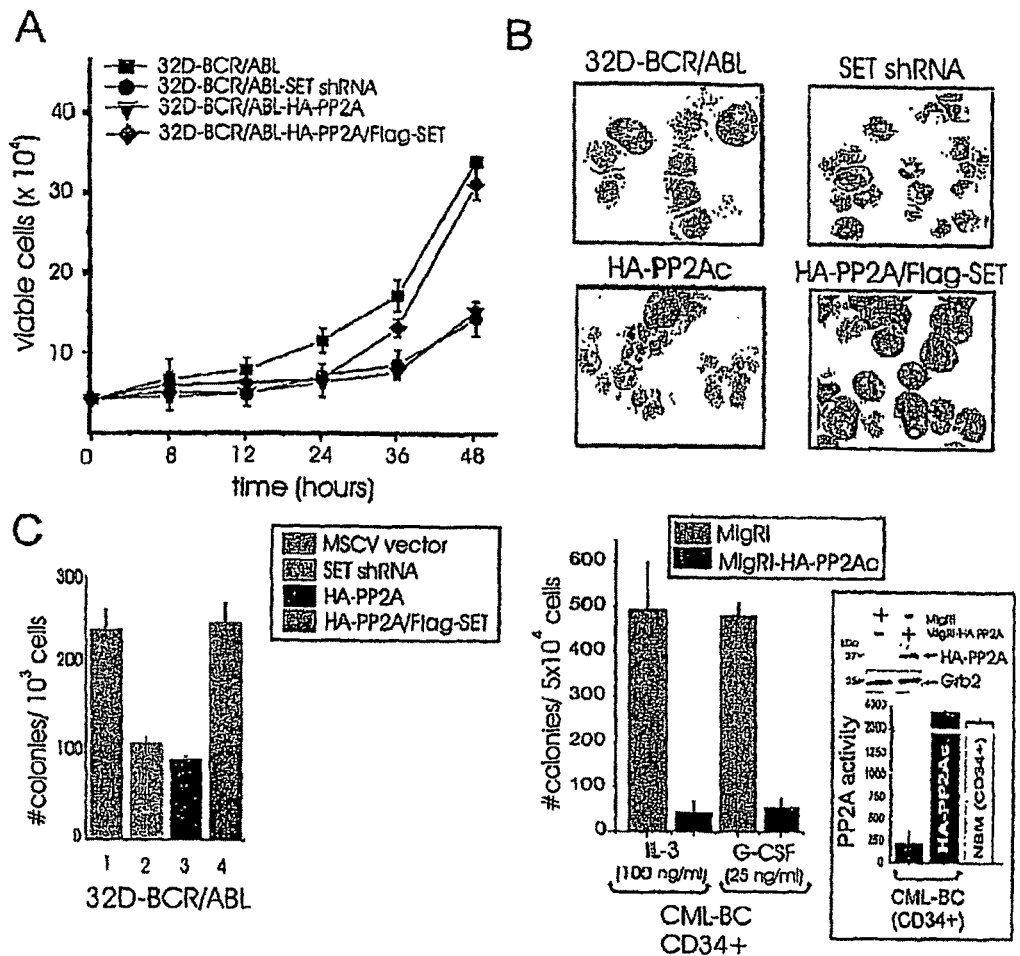
FIG. 5. In vitro effects of PP2Ac overexpression. A: Effect of ectopic SET shRNA, HA-PP2A, and HA-PP2A/FLAG-SET expression on the cytokine-independent growth of 32D-BCR/ABL. Each point of the graph represents the mean±SE of the number of viable cells from three independent experiments. B: May-Grunwald/Giemsa staining of cytospins of G-CSF-treated (9-12 days) 32D-BCR/ABL and derivative cell lines. C: Growth factor-independent colony-forming ability of parental cells and SET shRNA-, HA-PP2A-, and HA-PP2A/FLAG-SET-expressing 32D-BCR/ABL, and effect of ectopic PP2Ac expression on the IL-3- and G-CSF-driven colony formation of CML-BC$^{CD34+}$ (dark bars). Red bars indicate colonies from vector-transduced cells. Bars represent the mean±SD of three independent experiments (primary cells: n=2). Inset: expression of ectopic PP2Ac in GFP+ CML-BCCD34+ and PP2A activity in MigRI- and MigRI-HA-PP2Ac-transduced CML-BC$^{CD34+}$, and in CD34+ normal marrow cells (NBM).

To assess whether increased PP2A activity affects proliferation and survival of BCR/ABL-transformed cells, parental, SET shRNA-expressing, and HA-PP2A-expressing 32D-BCR/ABL cells were grown in the presence or absence of IL-3. In IL-3-containing medium, there were no differences in the growth of 32D-BCR/ABL and its derivative cell lines (data not shown). Between 36 and 48 hr after IL-3 withdrawal, an ~60% decrease in the number of viable cells was visible in SET shRNA- and HA-PP2A-expressing 32D-BCR/ABL when compared to parental cultures (FIG. 5A). Moreover, SET shRNA- and, to a greater extent, HA-PP2A-expressing 32D-BCR/ABL cells underwent granulocytic differentiation upon exposure (9-12 days) to G-CSF (FIG. 5B). As expected, forced FLAG-SET expression conferred a proliferation advantage and inhibited differentiation of HA-PP2A-expressing cells (FIGS. 5A and 5B). Similarly, reduced viability and spontaneous erythroid differentiation, observed in 1K562 cells ectopically expressing SET shRNA or HA-PP2A, was counteracted by SET overexpression (data not shown).

Note that SET overexpression did not confer cytokine-independent growth and slightly enhanced proliferation of 32Dc13 cells (FIG. 8C). Similarly, SET downregulation in 32Dc13 cells did not alter IL-3-dependent proliferation, consistent with the observation that SET shRNA expression did not affect PP2A activity in 32Dc13 cells (FIGS. 8B and 8C).

The importance of suppression of PP2A activity for BCR/ABL leukemogenesis was further investigated by assessing the colony-forming ability of SET shRNA-, HA-PP2A-, and HA-PP2A/FLAG-SET-expressing BCR/ABL+ cell lines. Similarly, CML-BC$^{CD34+}$ patient cells transduced with a MigRI-HA-PP2Ac or insert-less retrovirus were GFP sorted and plated in methylcellulose in the presence of cytokines. 32D-BCR/ABL (FIG. 5C) and K562 (data not shown) cells formed high numbers of colonies in the absence of growth factors (FIG. 5C). By contrast, the colony-forming ability of SET shRNA- and HA-PP2A-expressing cells was markedly suppressed (60%-65% inhibition) (FIG. 5C), and the colony size was much smaller than that of parental cells (data not shown). Consistent with its role as a PP2A inhibitor, SET overexpression completely rescued the cytokine-independent colony-forming ability of HA-PP2A-expressing BCR/ABL cell lines (FIG. 5C). Accordingly, HA-PP2Ac expression restored PP2A activity back to normal levels (FIG. 5C, inset in right panel) and reduced by ~90% the clonogenic potential of CML-BC$^{CD34+}$ cells (FIG. 5C, right panel).

Figure 6:
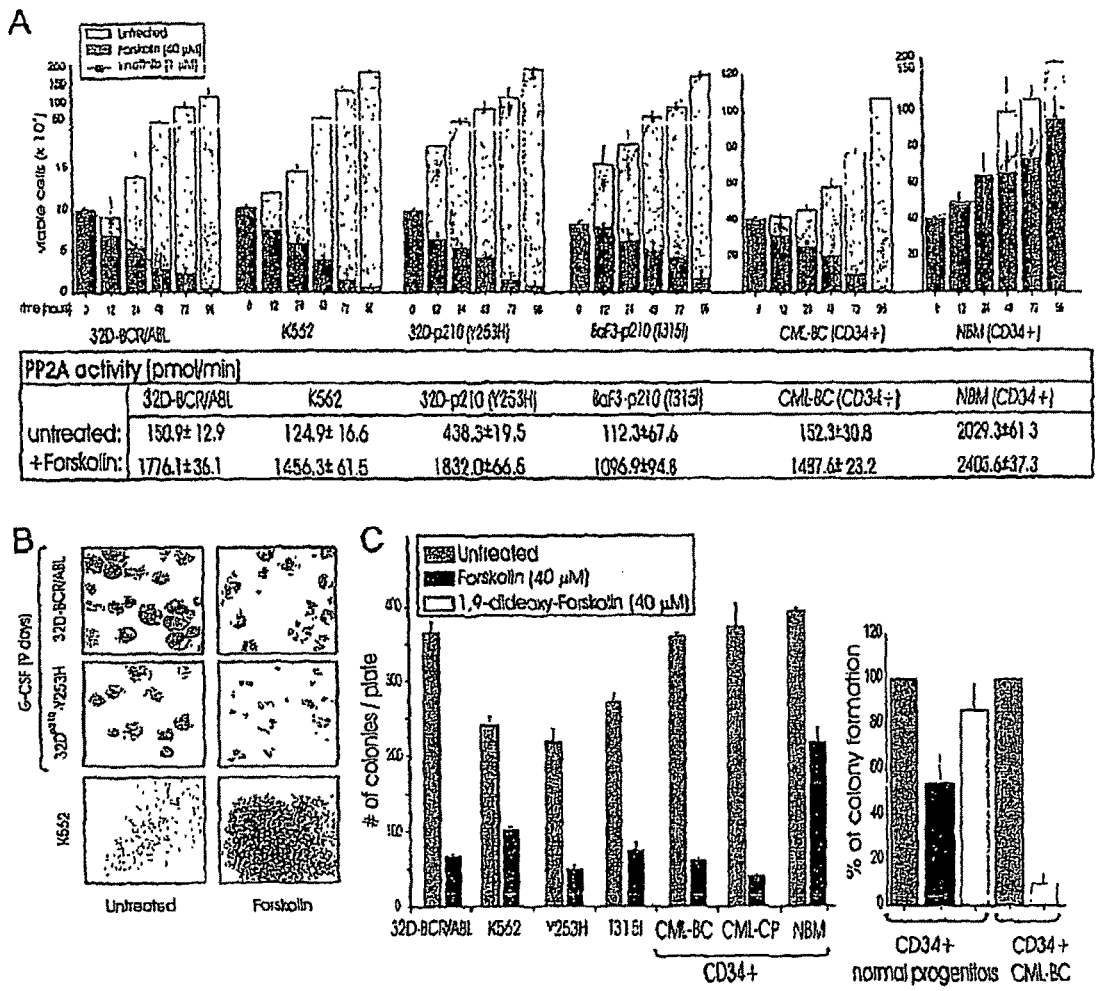
FIG. 6. In vitro effects of forskolin on BCR/ABL oncogenic potential. A: Effect of the PP2A activator forskolin (dark bars) and of imatinib (red lines) on the growth of imatinib-sensitive and -resistant BCR/ABL+ cell lines and of primary CML-BC$^{CD34+}$ (n=2) and NBM$^{CD34+}$ (n=2) cells; untreated cells (light bars). Effect of forskolin on PP2A activity is shown below each graph. Viable cells and phosphatase activity in untreated and drug-treated cell lines and primary cells (n=2) are expressed as mean±SE of three independent experiments. B: May-Grunwald/Giemsa staining of G-CSF-treated 32D-BCR/ABL and imatinib-resistant 32D-p210$^{Y253H}$ cells; o-Dianisidine staining of untreated and forskolin-treated (48 hr) K562 cells. C: Methylcellulose colony formation (expressed as mean±SE of the colony number from three clonogenic assays) of untreated (red bars), forskolin-treated (black bars), and 1,9-dideoxy-forskolin-treated (yellow bars) imatinib-sensitive and -resistant BCR/ABL cell lines, and cytokine-driven colony formation of primary CML-BC$^{CD34+}$ (n=2), CML-CP$^{CD34+}$ (n=2), and normal (NBM) (n=2) CD34+ cells.

Antileukemic Effects of Forskolin in Primary CML-BC$^{CD34+}$ Cells and in Imatinib-Sensitive and -Resistant BCR/ABL Cell Lines To investigate whether inhibition of BCR/ABL activity/expression by pharmacological activation of PP2A (FIG. 3B) correlates in vitro with impaired BCR/ABL leukemogenic potential, 32Dc13, NBM$^{CD34+}$, 32D-BCR/ABL, K562, the imatinib-resistant 32D-p210$^{Y253H}$ and BaF3-p210$^{T315I}$, and CML-BC$^{CD34+}$ patient cells were treated with the PP2A activator forskolin (40 μM; 96 hr). Forskolin strongly augmented PP2A phosphatase activity in all BCR/ABL cell lines and primary CML-BC$^{CD34+}$ blasts (FIG. 6A) but not in 32Dc13 (FIG. 8B) or in NBM$^{CD34+}$ cells (FIG. 6A). While untreated cells grew with normal kinetics (FIG. 6A, light bars), forskolin treatment resulted in marked suppression of cell growth and enhanced apoptosis (FIG. 6A, dark bars) of cytokine-deprived imatinib-sensitive and -resistant BCR/ABL+ cell lines and of IL-3/IL-6/Flt-3 ligand/c-Kit ligand-cultured CML-BC$^{CD34+}$ patient cells.

Figure 10:
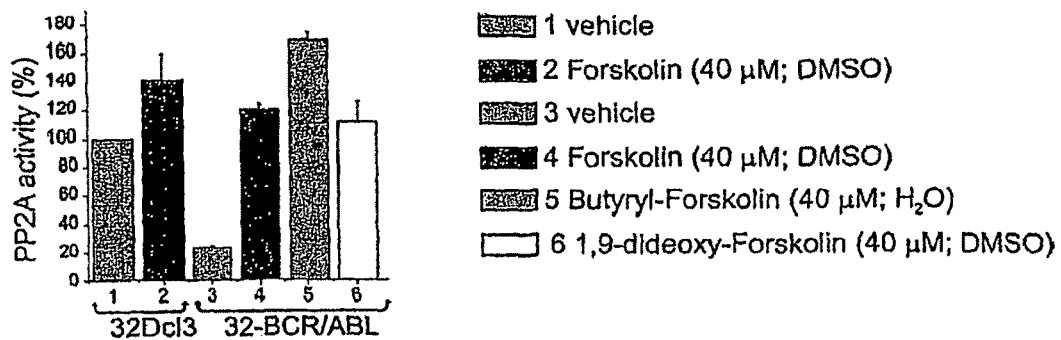
FIG. 10. Pro-apoptotic and PP2A-inducing effects of forskolin and its derivatives in different BCR/ABL-expressing cell lines and primary marrow CML cells. A: Effect of forskolin and its derivative compounds on PP2A phosphatase activity. Histogram shows effect of forskolin (40 µM; 48 hours) on PP2A activity in parental and BCR/ABL-expressing 32Dc13 cells (lanes 1-4), and effect of the water soluble Butyryl-forskolin (lane 5) and of the 1,9-dideoxy-forskolin (lane 6) that lacks adenylate cyclase activating function. B: Pro-apoptotic effects of forskolin and its derivative compounds. Plots show Annexin V/PI staining of DMSO- or forskolin-treated parental 32Dc13 myeloid progenitors, imatinib-sensitive (32D-BCR/ABL) and imatinib-resistant (BaF3-p210 T315I) cell lines, and of CD34+ normal marrow cells (NBM) and CD34+ CML-blast crisis marrow cells (CML-BC). The pro-apoptotic effect of butyryl-forskolin and 1,9-dideoxy-forskolin has been also assessed in 32D-BCR/ABL cells. Numbers (red), in each plot, indicate the percentage of cells positive to annexin-V (sum of the cells present in the lower and upper right panels) staining. Note that forskolin does not induce apoptosis in non-transformed myeloid progenitor cell lines and CD34+ primary marrow cells.
Figure 10:
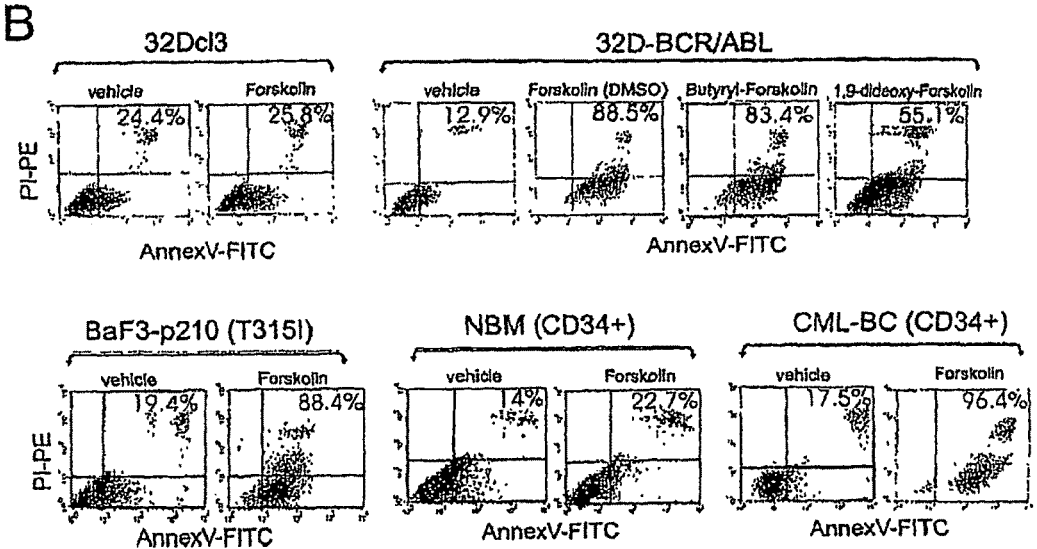
Figure 11:
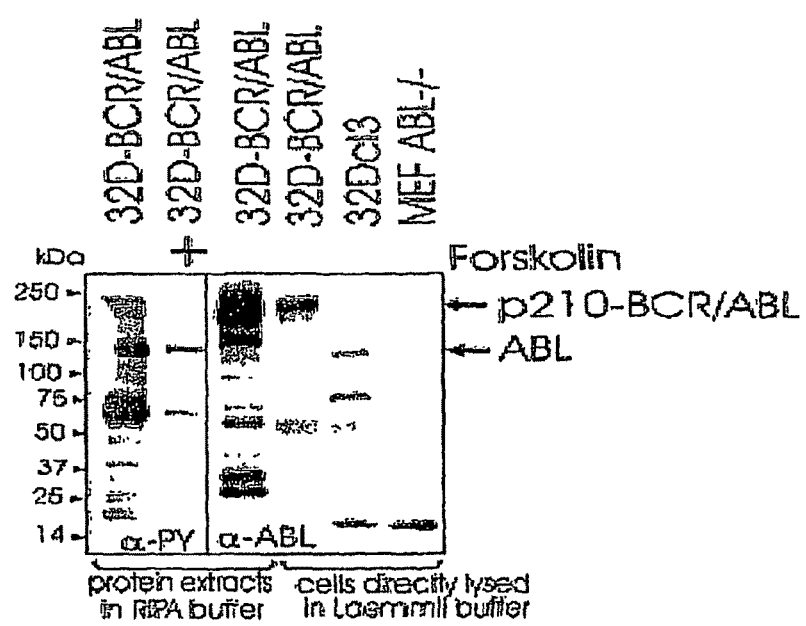
FIG. 11. BCR/ABL and ABL expression in 32Dc13, 32D-BCR/ABL and ABL$^{-/-}$ MEF cells. Western blots show ABL expression and/or p210-BCR/ABL expression and tyrosine phosphorylation in 32Dc13, 32D-BCR/ABL (untreated or forskolin-treated) and ABL$^{-/-}$ MEF (kind gift of Dr. Koleske A., Yale University, CT) cells directly lysed in Laemmli buffer (3×105 cells/30 µl) or on 100 µg of protein lysates extracted in RIPA buffer (150 mM NaCl, 1% NP-40, 0.1% SDS, 50 mM Tris).

The effect of imatinib (1 μM) paralleled that of forskolin in imatinib-sensitive, but not resistant, BCR/ABL+ cells (FIG. 6A, red lines). Note that, after 48 hr of forskolin treatment, the percentage of apoptosis (annexin V+ cells) in BCR/ABL+ cell lines and primary CML-BC cells was 80% and 95%, respectively (FIG. 10B). By contrast, forskolin treatment neither inhibited IL-3-dependent growth nor induced apoptosis of 32Dc13 cells (FIGS. 8C and 10B). Notably, in primary NBM$^{CD34+}$ cells, forskolin partially inhibited cytokine-dependent proliferation to the same extent as imatinib (FIG. 6A) without inducing apoptosis (FIG. 10B). Indeed, cell cycle analysis of forskolin-treated (24 hr) NBM$^{CD34+}$ cells revealed an increased number of cells in G1 and a reduced number in S phase (data not shown).

Restored differentiation was another feature exhibited by forskolin-treated cells; after 9-12 days of exposure to G-CSF and forskolin, cell death was evident in 30%-40% of both imatinib-sensitive 32D-BCR/ABL and -resistant 32D-p210Y253H cell cultures, whereas the remaining 60%-70% showed signs (e.g., segmented nuclei) of terminal neutrophilic differentiation (FIG. 6B, right panels). By contrast, cells exposed only to G-CSF remained blasts and proliferated (FIG. 6B, left panels). Seemingly, forskolin-treated K562 cells underwent erythroid differentiation (FIG. 6B).

Regardless of the degree of responsiveness to imatinib, both sensitive and resistant BCR/ABL+ cell lines showed inhibition (average: 75%) of clonogenic potential when exposed to forskolin (FIG. 6C). Accordingly, forskolin strongly abolished (80%-90% inhibition) the ability of primary CML-BC$^{CD34+}$ and CML-CP$^{CD34+}$ marrow cells to form IL-3-derived colonies in semisolid medium (FIG. 6C). In addition, the colonies derived from forskolin-treated cells were also reduced in size (data not shown), thus resembling the effects of PP2A overexpression on the colony-forming ability of BCR/ABL+ cells. Moreover, levels of BCR/ABL phosphorylation in residual colonies derived from forskolin-containing cultures were comparable to those from colonies of untreated BCR/ABL cells (data not shown), suggesting that a decrease in forskolin activity occurring in 15 days of semisolid culture accounts for the presence of residual colonies.

Although forskolin did not induce apoptosis of NBM$^{CD34+}$ cells, a 40%-50% decrease in their IL-3-dependent clonogenicity was observed upon exposure to forskolin (FIG. 6C). Interestingly, the PP2A activator 1,9-dideoxy forskolin, which lacks adenylate cyclase-activating function, had only a modest (≤15%) effect on cytokine-driven colony formation of CD34+ myeloid progenitors, whereas it induced a 85%-90% decrease in the clonogenic potential of CML-BC$^{CD34}$+ cells (FIG. 6C).

EXAMPLE 2

In-Vivo Studies of Anti-Leukemic Agents in SCID Mice

Figure 7:
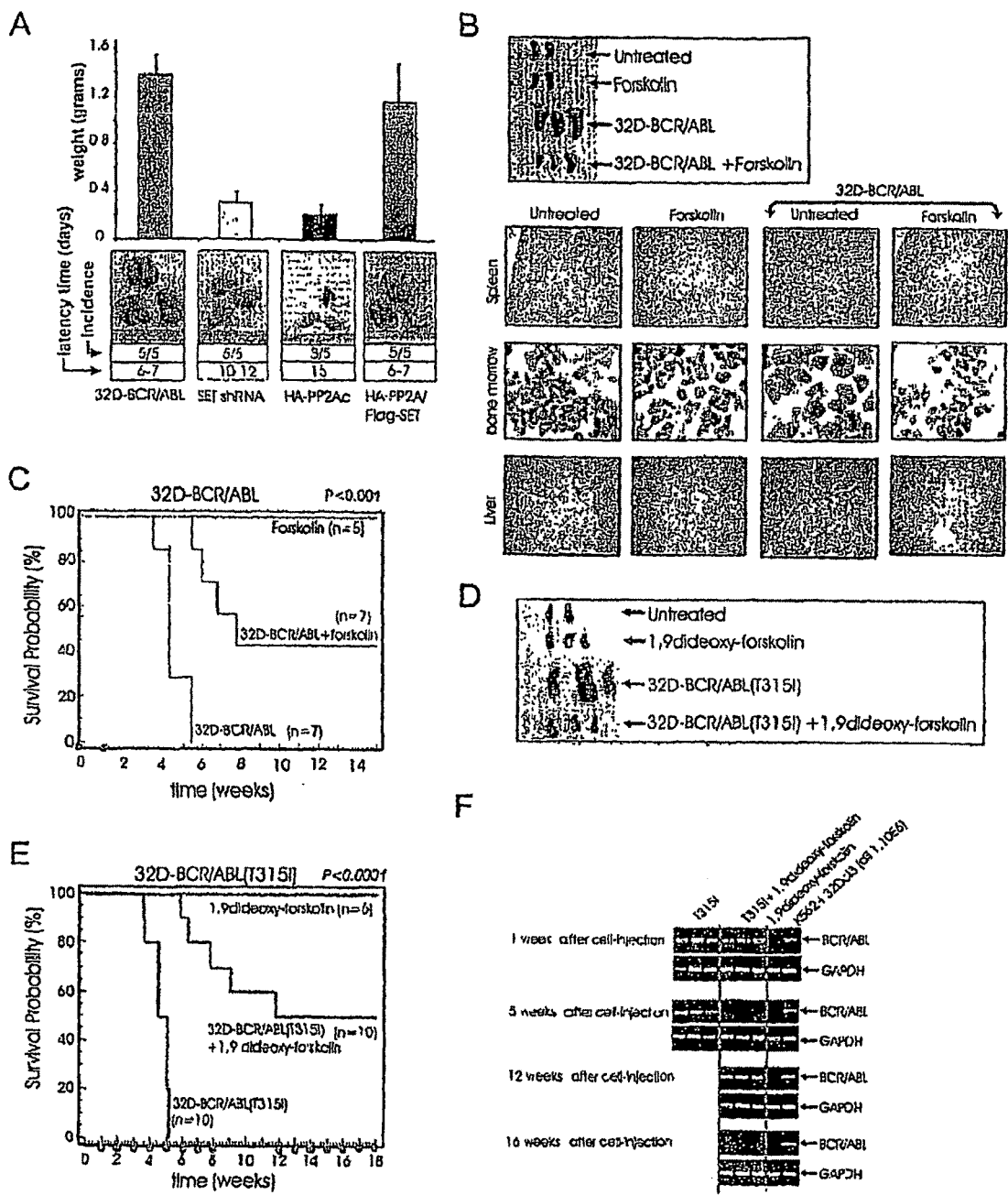
FIG. 7. In vivo effects of PP2A activation on wild-type and T315I BCR/ABL leukemogenesis. A: Tumors in SCID mice arising from subcutaneous injection of parental and derivative 32D-BCR/ABL cell lines. Latency time, incidence, and tumor weight (mean±SD) were calculated. (p<0.01; Kruskal-Wallis test). B (top) and D: Representative visual analysis of spleens of untreated and drug-treated mice injected or not injected with BCR/ABL+ cells. B (bottom): Hematoxylin/eosin staining of tissue sections from spleen, marrow, and liver. C: Effect of forskolin on survival of SCID mice i.v. injected with 32D-BCR/ABL cells. Estimate survival probabilities were calculated by the Kaplan-Meier method (overall: p<0.001; 32D-BCR/ABL versus 32D-BCR/ABL+forskolin: p<0.001; log-rank test). E: Effect of 1,9-dideoxy forskolin on BCR/ABL(T315I)-mediated leukemogenesis. SCID mice were treated 1-8 and 12-18 weeks after i.v. injection with 5×105 cells. Mice injected with cells or drug only served as controls. Survival probability was calculated by the Kaplan-Meier method (p<0.0001; log-rank test). F: Nested RT-PCR for BCR/ABL indicates the presence of 32D-BCR/ABL(T315I) cells in peripheral blood of untreated and drug-treated mice. The last two lanes (negative and positive control, respectively) show nested RT-PCR performed with RNA from blood of mice treated with drug only and from K562: 32Dc13 cells. Detection of GAPDH mRNA was used as control. Red dots indicate the time of drug injection FIG. 8. Role of SET expression in normal CD34+ marrow and 32Dc13 cells. A: Effect of cytokine(s) on SET expression. Western blots show SET and Grb2 expression in: 1) Parental and BCR/ABL-expressing 32Dc13 cells maintained in culture in the presence of IL-3 (lanes 1 and 4) or IL-3-deprived for 12 hours (lanes 2 and 5) or in 32D-BCR/ABL treated with 1 µM imatinib for 24 hours (lane 3); 2) The CD34+ fraction of normal bone marrow cells (NBM) maintained in culture in the presence of IL-3/IL-6/KL/Flt3 ligand (lane 6) used at the concentrations indicated in the text (see Experimental Procedures) or cytokine-deprived for 12 hours (lane 7). B: PP2A phosphatase activity in 32Dc13 and derivative cell lines. The histogram shows the effect of treatment with the PP2A activator forskolin (40 µM; 48 hours treatment) (lane 2), and of ectopic SET shRNA (lane 3) and Flag-SET (lane 4) expression on PP2A activity in 32Dc13 cells. Untreated parental 32Dc13 (lane 1) and 32D-BCR/ABL cells (lane 5) were used as control. C: Effect of ectopic SET expression, SET knock-down and forskolin-treatment on cytokine-dependent proliferation and survival of parental 32Dc13 cells. In 32Dc13 cells, forskolin treatment and up- or down-regulation of SET expression did not significantly affect cytokine-dependent growth and/or apoptosis induced by IL-3-deprivation.

Results: To investigate the effect of PP2A on BCR/ABL tumorigenesis, SCID mice (n=5 per group) were injected subcutaneously with parental cells or SET shRNA-, HA-PP2Ac-, or HA-PP2A/FLAG-SET-expressing 32D-BCR/ABL cells. 32D-BCR/ABL and 32D-BCR/ABL-HA-PP2A/FLAG-SET cells formed tumors (incidence: 5/5) in 6-7 days, whereas tumors from SET shRNA-expressing 32D-BCR/ABL cells were palpable (incidence: 5/5) only after 10-12 days postinjection (FIG. 7A). By contrast, tumors from HA-PP2A-expressing 32D-BCR/ABL cells were at most barely palpable (incidence: 3/5) and, at 15 days postinjection, weighed 86%-90% less than the tumors derived from parental or HA-PP2A/FLAG-SET-expressing 32D-BCR/ABL cells (FIG. 7A). Likewise, a 75% decrease in tumor mass was observed in mice injected with SET shRNA-expressing 32D-BCR/ABL cells.

To determine if forskolin ($LD50_{i.p.}$=67 mg/kg) can attenuate BCR/ABL leukemogenesis, SCID mice were intraperitoneally (i.p.) treated with forskolin (4 mg/kg) 1 hr prior to and 7 days after the intravenous (i.v.) injection of 32D-BCR/ABL cells ($5\times10^5$ cells/mouse) and compared with mice injected either with cells or with forskolin only. Four weeks later, various organs obtained from untreated, treated, and control groups were evaluated by visual inspection and light microscopy. Mice injected with parental 32D-BCR/ABL cells (n=3) showed massive splenomegaly, whereas morphology of spleens from forskolin-treated 32D-BCR/ABL-injected mice (n=3) resembled that of control age-matched (n=2) or forskolin-only (n=2) treated mice (FIG. 7B). Hematoxylin/eosin-stained sections of spleen, marrow, and liver of vehicle-treated 32D-BCR/ABL-injected mice showed extensive infiltration of blasts with a low degree of myeloid maturation typical of an overt acute myeloid leukemia-like process (FIG. 7B). In contrast, histopathology of organs from the forskolin-treated 32D-BCR/ABL-injected group (FIG. 7B) was similar to that of the age-matched and forskolin-injected control groups. Consistent with these findings, the survival of forskolin-treated mice injected with 32D-BCR/ABL cells was significantly longer (median: 8 weeks) than that of mice injected with cells only (median: 4 weeks) (FIG. 7C). At 15 weeks postinjection, 40% of forskolin-treated cell-injected mice and 100% of control mice that received only forskolin were still alive with no sign of toxic side effects (data not shown). By contrast, modest to severe splenomegaly and leukemic infiltration of hematopoietic organs were evident in drug-treated BCR/ABL mice that died 5 or more weeks after cell injection (data not shown).

In similar experiments, 26 SCID mice were i.v. injected ($5\times10^5$ cells/mouse) with 32D-BCR/ABL cells expressing the imatinib-, AMN107-, and BMS354825-resistant T315I BCR/ABL mutant. After 8 days, treatment with 1,9-dideoxy forskolin (8 mg/kg/week; i.p.; $LD_{50}$=68 mg/kg) was initiated on 13 mice upon determining the presence of circulating BCR/ABL$^+$ cells by nested RT-PCR-mediated detection of BCR/ABL transcripts in the peripheral blood (FIG. 7F, first panel). After 4 weeks of treatment, drug-treated leukemic mice were all alive and BCR/ABL negative (FIGS. 7E and 7F), whereas only 3 untreated leukemic mice were alive but appeared lethargic and were BCR/ABL$^+$ (FIG. 7F, second panel). Thus, a representative sample of each group of mice was sacrificed, and various organs were evaluated for signs of leukemia. Splenomegaly (FIG. 7D) and infiltration of hematopoietic organs (data not shown) was observed in mice injected with T315I cells. By contrast, organ infiltration (data not shown) and splenomegaly were not present in drug-treated cell-injected mice (FIG. 7D). Because 70% of these mice were alive after 7 weeks of treatment, administration of the drug was suspended (FIG. 7E). Unexpectedly, 20% of mice relapsed and died of an acute leukemia-like disease process within 4 weeks from the end of treatment (FIG. 7E), and the remaining 50% tested BCR/ABL$^+$ (FIG. 7F, third panel). After 4 weeks from restarting therapy, 100% of treated mice (50% of cell-injected mice) became BCR/ABL negative and were alive 18 weeks after cell injection with no signs of toxic side effects (FIG. 7E) like the control age-matched or drug only-treated mice.

Materials and Methods: Parental cells and shRNA SET-, HA-PP2A-, and HA-PP2A/FLAG-SET-expressing 32D-BCR/ABL cells were injected ($5\times10^6$ cells/mouse) subcutaneously into 5-week-old SCID mice (Fox Chase SCID ICR; Taconic). Tumor growth was monitored every other day. Mice were sacrificed 15 days postinjection, and excised tumors were fixed in phosphate-buffered formalin. To determine the effect of forskolin and 1,9-dideoxy forskolin on in vivo BCR/ABL leukemogenesis, 6-week-old SOD mice were i.v. injected with $5\times10^5$ 32D-BCR/ABL or 32D-BCR/ABL (T315I) cells (10 to 13 mice/group) and treated with forskolin (100 µg/ml of 2% DMSO/PBS) or 1,9-dideoxy forskolin (200 µg/ml of 2% DMSO/PBS) using the indicated schedule. Age-matched mice or mice injected with cells or drugs only (6 to 7 mice) served as controls. Four weeks post-injection, 2 to 3 mice from each group were sacrificed, and organs were analyzed for the presence of leukemia. At the indicated times, the disease process was monitored by nested RT-PCR-mediated BCR/ABL detection using peripheral blood collected by lateral tail-vein incision. For pathological examination, tissue sections from bone marrow, spleen, and liver were fixed in formalin, embedded in paraffin blocks, and hematoxylin/eosin stained. The remaining mice were used for survival studies, which were terminated 15-18 weeks postinjection. The in vitro and in vivo animal studies were conducted with the approval of the Ohio State University Institutional Lab Animal Care and Use Committee and in accordance with the National Institute of Health guidelines for animal care.

EXAMPLE 3

PP2A Activators in Philadelphia Positive Acute Lymphoblastic Leukemia (Ph1-ALL)

Another disease mediated by BCR/ABL is Ph$^1$-positive ALL. Currently there are no therapeutic agents in the clinic that activate PP2A for Ph$^1$-ALL making PP2A activation a highly relevant therapeutic target for clinical use. Additionally, despite in vitro efficacy of imatinib against p190-BCR/ABL-transformed cells, clinical trials have shown limited or no efficacy in patients, who overall show a poor prognosis. We studied the in vitro effect of Forskolin and other PP2A activators on proliferation rate, clonogenic potential, and apoptosis in p190-BCR/ABL-expressing ALL cells.

Figure 12:
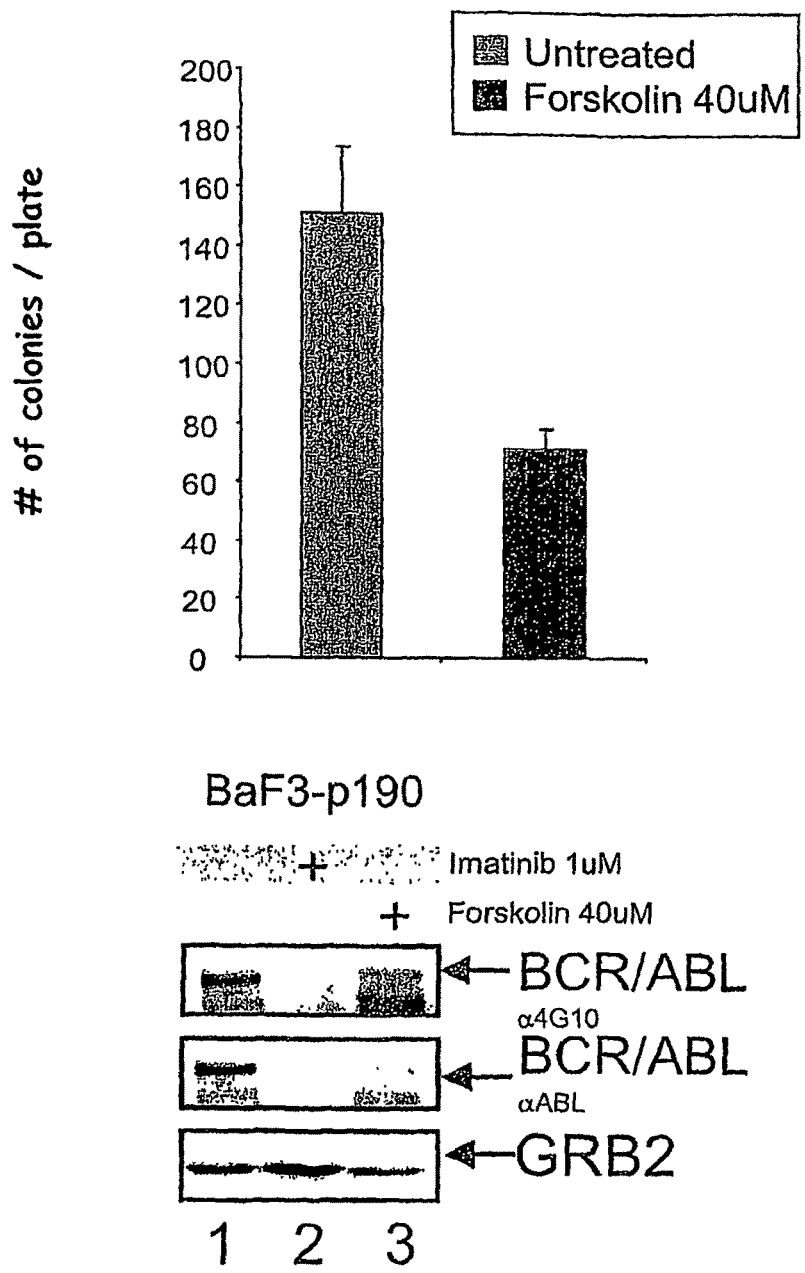
FIG. 12. In vitro effect of forskolin on BaF3-P190 Cells. Top: Effect of Forskolin (40 µM) on cytokine-independent colony-forming ability of the BaF3-p190 cell line. Bottom: Effect of Forskolin (40 µM) and imatinib (1 µM) on p190$^{BCR/ABL}$ activity (α4G10) and expression (αABL). Grb2 levels were detected as a control.

In vitro studies of BaF3 p190-BCR/ABL-expressing cells demonstrated significant growth inhibition, apoptosis and impaired clonogenic potential (FIG. 12). Our previous studies have demonstrated that Forskolin induces PP2A activity in BCR/ABL-transformed cell lines prior to induction of apoptosis. Induction of PP2A activity occurs without increased expression of PP2A protein levels. As a consequence of PP2A activation upon treatment with Forskolin BCR/ABL undergoes inactivation/degradation.

Our studies show that Forskolin and other PP2A activators may be evaluated as therapeutic agents in Philadelphia positive malignancies, including Ph$^1$-ALL. Forskolin mediates cell death through its ability to activate PP2A phosphatase and therefore induce BCR/ABL inactivation.

EXAMPLE 4

FTY720 as an Anti-Leukemic Agent

FTY720 is a small molecule currently being developed for use as an immunosuppressive agent following organ transplantation. FTY720 is a synthetic analogue of a natural compound derived from the fungus Isaria Sinclarii. FTY720 is an agonist of sphingosine receptor mediated signaling and thereby interferes with lymphocyte trafficking. We investigated FTY710 as a therapeutic agent for imatinib-sensitive and -resistant Philadelphia positive leukemias.

We studied the in vitro effect of FTY720 and derivative compounds on proliferation rate, clonogenic potential, and apoptosis in imatinib-sensitive and -resistant p210-BCR/ABL-expressing cells and p190-BCR/ABL-expressing cells. We then investigated the in vivo antileukemic potential of FTY720 in a mouse-model of imatinib-resistant CML-BC, We obtained FTY720 synthesized using previously published methods (see Budde, K., et al., First human trial of FTY720, a novel immunomodulator, in stable renal transplant patients. *J Am Soc Nephrol*, (2002) 13:1073-83). Cells in liquid culture and in methylcellulose colony assays were cultured in the presence of 2.5 μM FTY720. SCID mice were i.v. injected with $5\times10^5$ T315I BCR/ABL-transduced 32Dc13 cells and levels of BCR/ABL in the peripheral blood were assessed by nested reverse transcriptase PCR. Upon establishment of a leukemia-like disease, mice were i.p. injected daily with FTY720 (250 μg/mouse/day). The disease process was monitored weekly by nested reverse transcriptase PCR. Apoptosis was assessed by AnnexinV/PI staining on untreated vs. treated cells.

Figure 13:
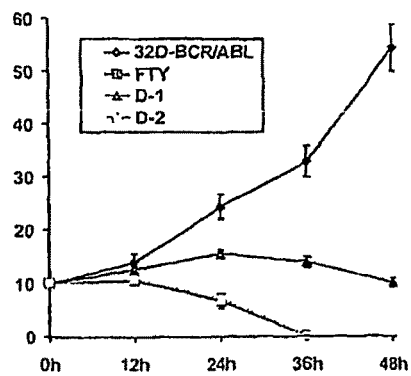
FIG. 13. In vitro effects of FTY720 and its derivative compounds on BCR/ABL oncogenic potential. Top Panels: Effect of FTY720 and derivatives D-1 and D-2 (all used at 2.5 µM) on cytokine-independent proliferation and survival of the imatinib-sensitive 32D-BCR/ABL cell line (left) and the imatinib-resistant 32D-BCR/ABL-T315I cell line (right). Middle Panels Effect of FTY720 and derivatives D-1 and D-2 (all used at 2.5 µM) on cytokine-independent colony-forming ability of the imatinib-sensitive 32D-BCR/ABL (left) and K562 (right) cell lines and the imatinib-resistant 32D-BCR/ABL-T315I cell line (center). Bottom Panels: Effect of FTY720 (2.5 µM) on cytokine-dependent colony-forming ability of primary CML-BC$^{CD34+}$ and normal CD34$^+$ bone marrow (NBM) cells.
Figure 13:
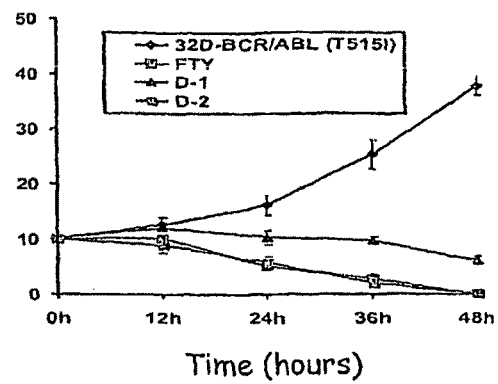
Figure 13:
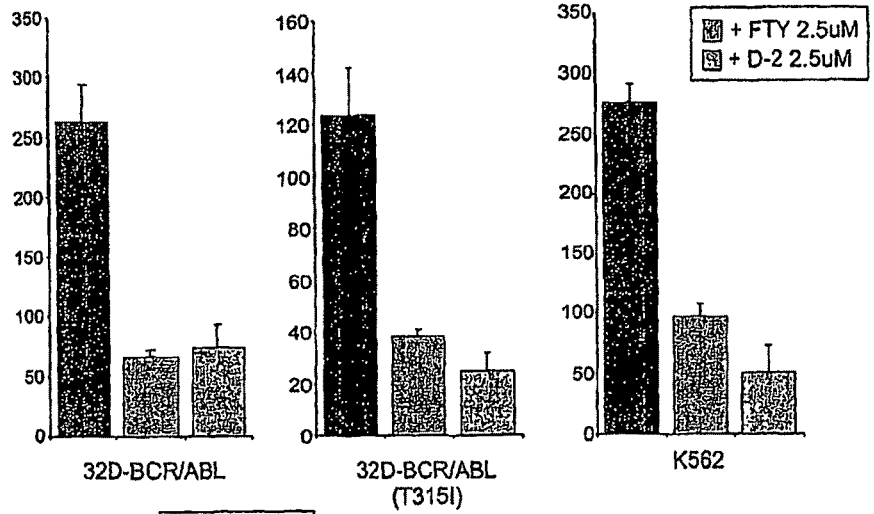
Figure 13:
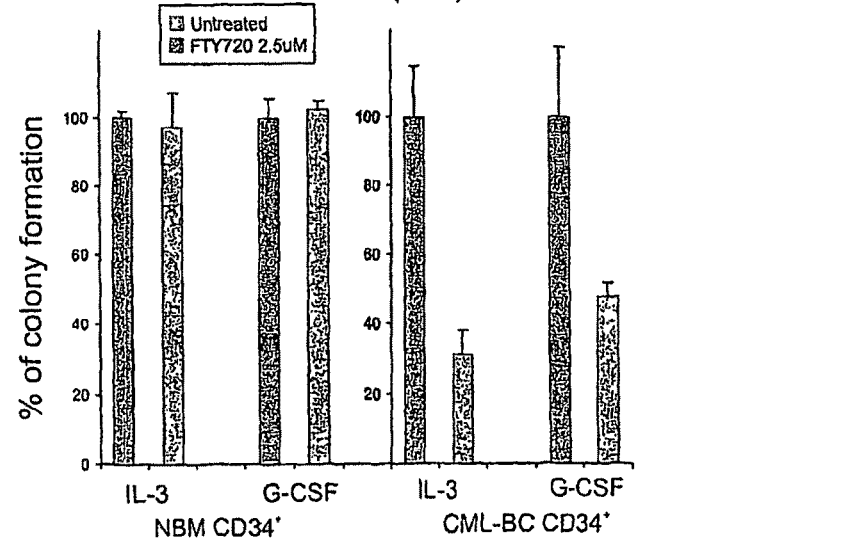
Figure 14:
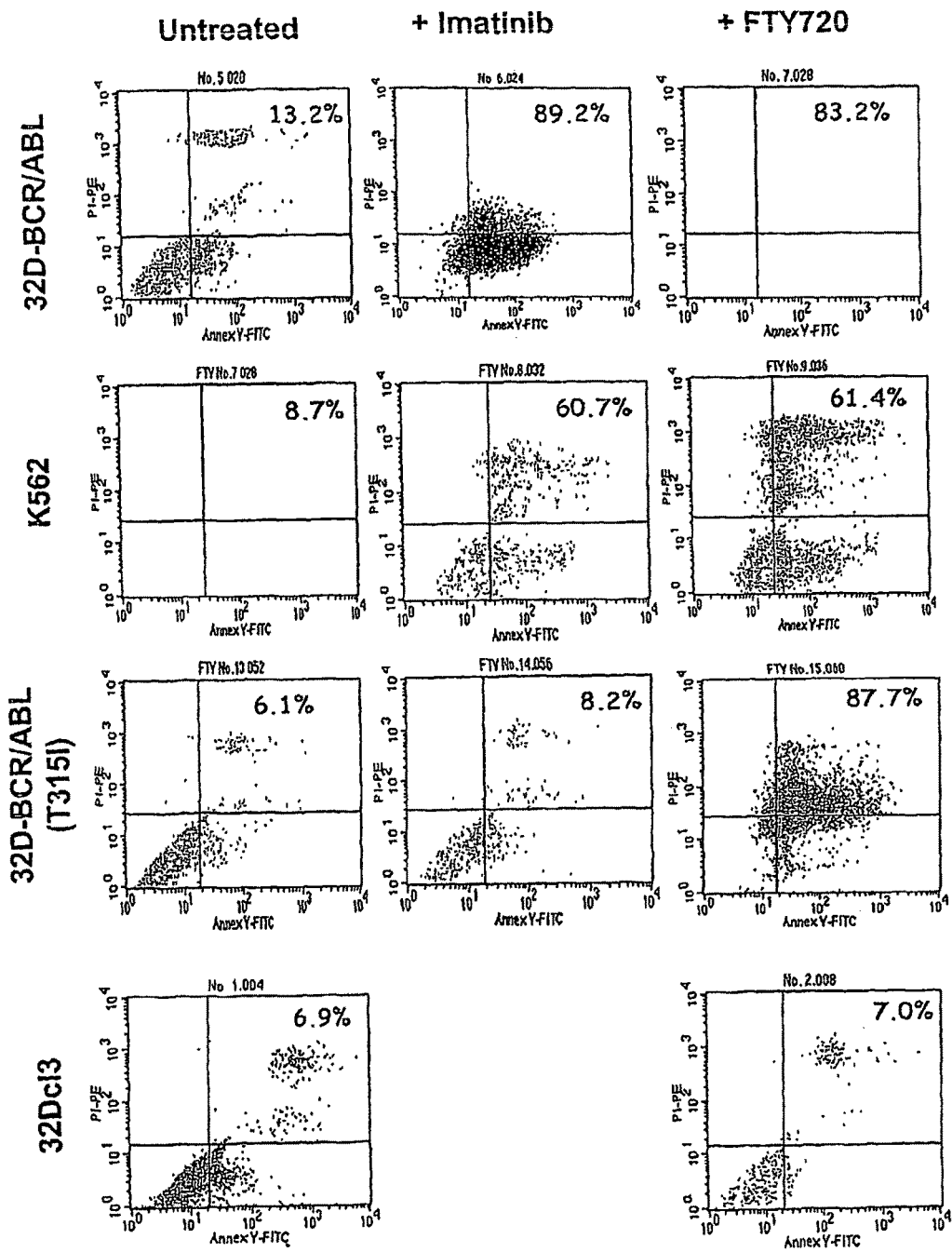
FIG. 14. Pro-apoptotic effects of FTY720 and its derivative compounds. Plots show Annexin V/PI staining of untreated or FTY720 (2.5 mM)-treated parental 32Dc13 myeloid progenitors, imatinib-sensitive (32D-BCR/ABL and K562) and imatinib-resistant (32D-BCR/ABL-T315I) cell lines. Numbers (red), in each plot, indicate the percentage of cells positive to annexin-V (sum of the cells present in the lower and upper right panels) staining.
Figure 15:
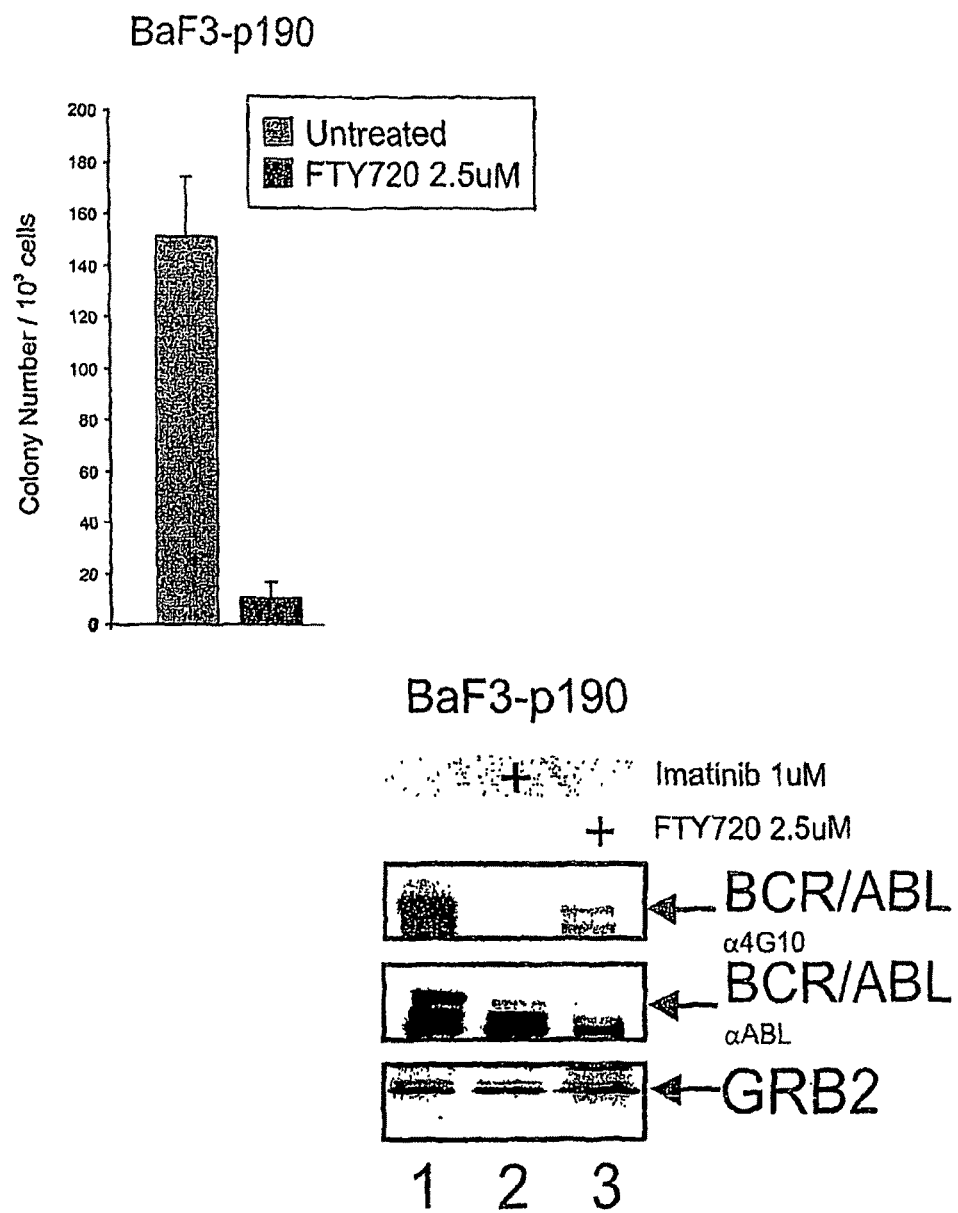
FIG. 15. In vitro effect of FTY720 and its derivative compounds on BaF3-P190 Cells. Top: Effect of FTY720 (2.5 µM) on cytokine-independent colony-forming ability of the BaF3-p190 cell line. Bottom: Effect of FTY720 (2.5 µM) and imatinib (1 µM) on p190$^{BCR/ABL}$ activity (α4G10) and expression (αABL). Grb2 levels were detected as a control.
Figure 16:
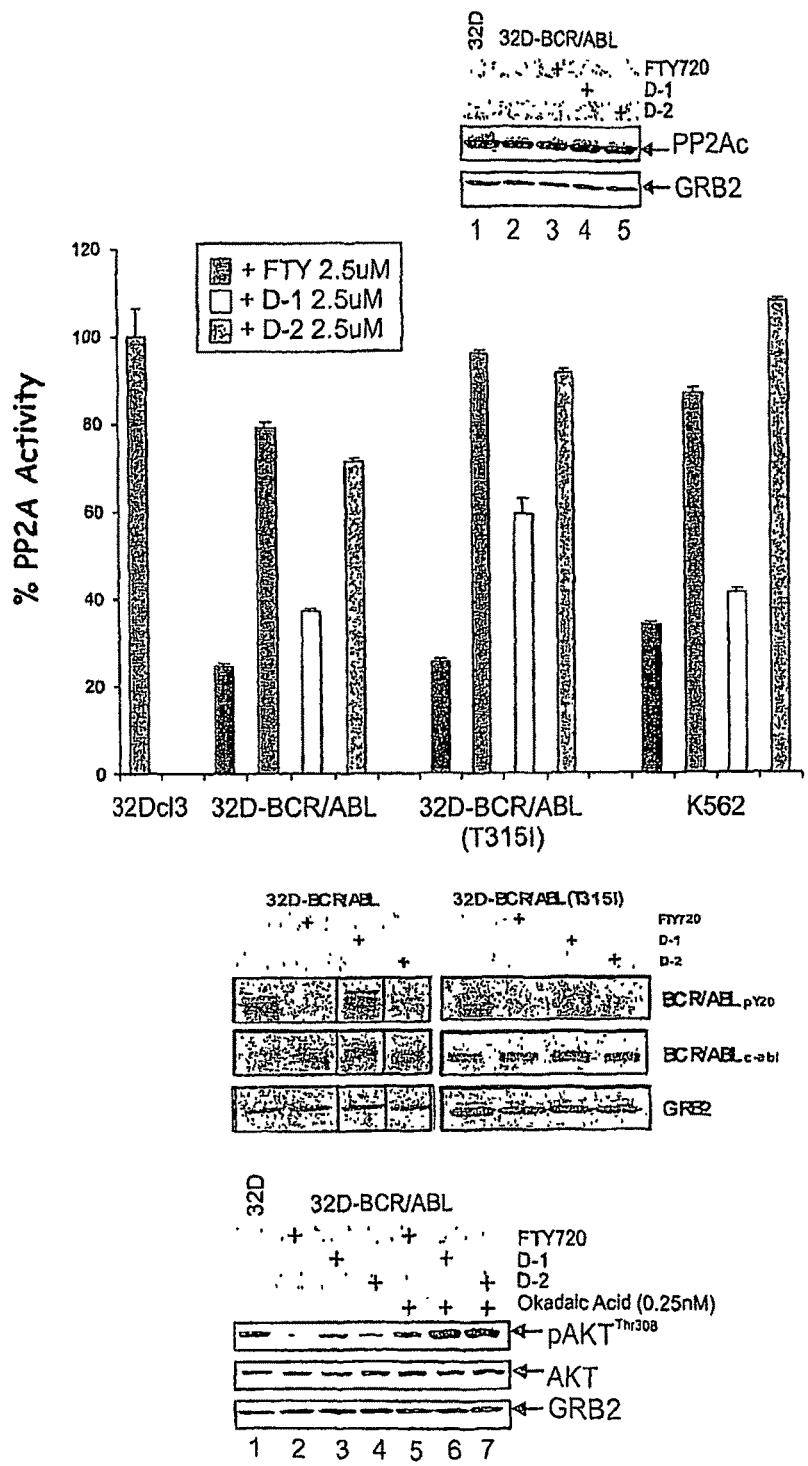
FIG. 16. In vitro effect of FTY720 and its derivative compounds on PP2A, BCR/ABL and Akt. Top: PP2A phosphatase assay in parental 32Dc13, 32D-BCR/ABL, 32D-BCR/ABL-T315I, and K562 cell line upon treatment with FTY720 and its derivative compounds (all used at 2.5 µM). Inset: Western blot shows levels of PP2Ac in 32Dc13 cells and in FTY720-treated 32D-BCR/ABL cells. Middle: Effect of FTY720 and its derivative compounds (2.5 µM) and imatinib (1 µM) on wild type- and T315I-BCR/ABL activity (αPY20) and expression (αABL). Grb2 levels were detected as a control. Bottom: Western blot shows levels of phosphorylated and total Akt in 32Dc13 cells and in untreated and FTY720 (2.5 mM)-treated 32D-BCR/ABL with or without the addition of okadaic acid (0.25 nM).
Figure 17:
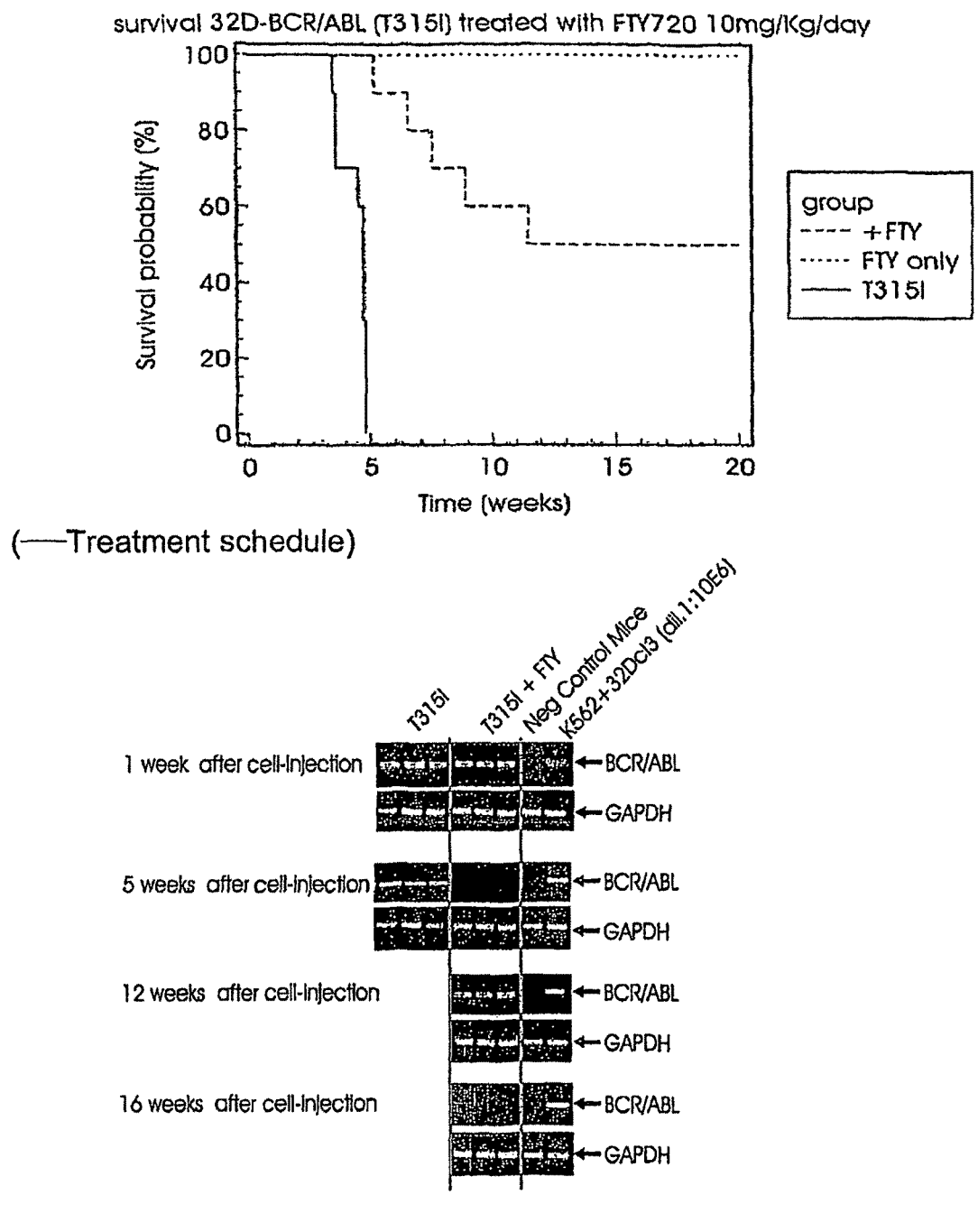
FIG. 17. In vivo effects of FTY720 and its derivative compounds on SCID mice. Top: Effect of FTY720 on survival of SCID mice i.v. injected with 32D-BCR/ABL (T315I) cells. Estimate survival probabilities were calculated by the Kaplan-Meier method (overall: p<0.0001; log-rank test). Mice injected with cells or drug only served as a control. Red lines indicate the length of the treatment. Bottom: Nested RT-PCR for BCR/ABL indicates the presence of 32D-BCR/ABL (T315I) cells in peripheral blood of untreated and drug-treated mice. The last two lanes (negative and positive controls, respectively) show nested RT-PCR performed with RNA from blood of mice treated with drug only and from K562:32 Dc13 cells. Detection of GAPDH mRNA was used as a control.
Figure 18:
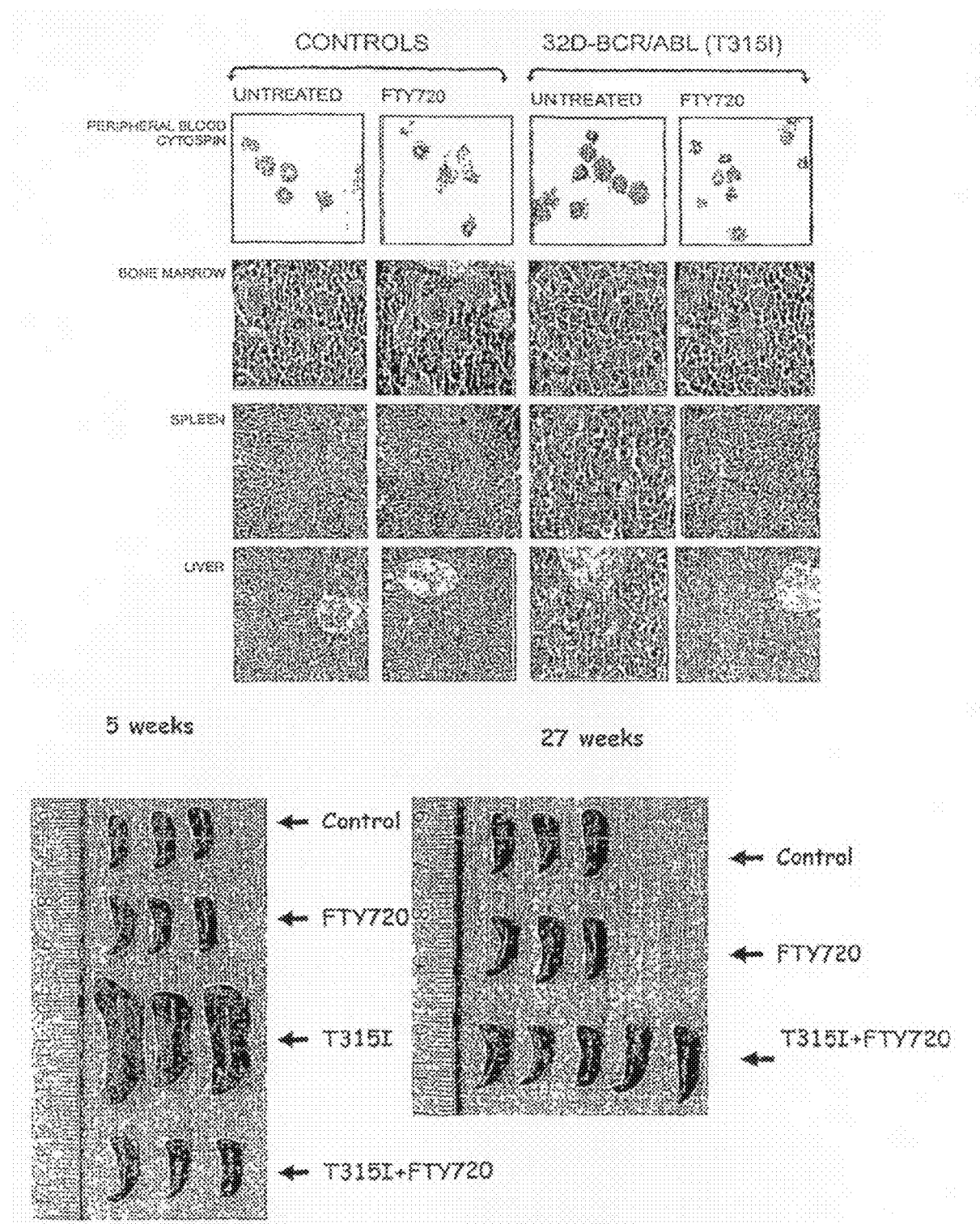
FIG. 18. In vivo effects of FTY720 and its derivative compounds on SCID mice. Top: Hematoxylin/eosin staining of cytospin from peripheral blood and tissue sections, of spleen, marrow, and liver. Bottom: Representative visual analysis at two different time points of spleens of untreated and drug-treated mice injected or non injected with 32D-BCR/ABL (T315I).

In Vitro studies against both primary CML-BC and imatinib-sensitive and -resistant p210-BCR/ABL expressing cell lines, and p190-BCR/ABL-expressing cell lines demonstrated significant growth inhibition, apoptosis and impaired clonogenic potential (FIG. 13-15). There was no difference in pre-clinical activity of FTY720 and published derivatives lacking immunosuppressive activity. Subsequent studies demonstrated that FTY720 induces PP2A activity in BCR/ABL-transformed cell lines prior to induction of apoptosis (FIG. 16). Induction of PP2A activity occurs without increased expression of PP2A protein levels. As a consequence of PP2A activation upon treatment with FTY720, BCR/ABL is inactivated (FIG. 16). Subsequent studies demonstrated that FTY720 susceptibility to apoptosis occurs as a consequence of inactivation of Akt (FIG. 16). Dephosphorylation and inactivation of Akt is a consequence of PP2A activation by FTY720. Inhibition of PP2A activation by okadaic acid abrogates in part the apoptosis and the effect on PP2A targets (e.g. Akt dephosphorylation) observed with FTY720 suggesting this in part explains the cell death induced by this agent (FIG. 16). The inhibitory effect of FTY720 on BCR/ABL-transformed cells, both primary and imatinib-sensitive and -resistant cell lines, appears to be selective only to those cells expressing the oncogene, as no effect was detected on untransduced 32Dc13 cells and on primary normal bone marrow cells from healthy donors (FIGS. 13 and 16). Moreover, in vivo studies have underlined the positive effect of FTY720 treatment in antagonizing and modulating the leukemic-like process induced in SCID mice intravenously injected with imatinib-resistant (T315I clone) BCR/ABL transformed cells; more than 50% of the mice i.v. injected with cells that received FTY720 were alive after 20 weeks of treatment, whereas all untreated mice died within the first month; importantly, no signs of toxicity were observed in the control group that received only the drug (FIGS. 17 and 18).

These studies suggest that FTY720 is a highly promising therapeutic agent for imatinib-sensitive and -resistant Philadelphia positive malignancies including CML (chronic and blastic phase) and $Ph^1$-ALL. FTY720 mediates cell death through its novel ability to activate PP2A phosphatase activity and therefore induce Akt and BCR/ABL inactivation. Currently there are no therapeutic agents in the clinic that activate PP2A for imatinib-sensitive and -resistant Philadelphia-positive leukemias, both CML and $Ph^1$-ALL making this a highly relevant therapeutic for clinical use.

What is claimed is:

1. A method for treating a BCR/ABL-mediated leukemia in a mammal consisting of administering to said mammal a therapeutically effective amount of a PP2A activating compound selected from the group consisting of protamine sulfate; rolipram; butyryl-forskolin; 1,9-dideoxy-forskolin; and FTY720; wherein the PP2A activating compound is optionally administered with a pharmaceutically acceptable carrier.

2. The method of claim 1, wherein the BCR/ABL-mediated leukemia is chronic myelogenous leukemia or Philadelphia positive acute lymphoblastic leukemia.

3. The method of claim 1, wherein the mammal is in the blast crisis stage of chronic myelogenous leukemia.

4. The method of claim 1, wherein the mammal is resistant to imatinib therapy.

5. The method of claim 1, wherein the mammal has refractory leukemia.

* * * * *